US006951839B1

(12) United States Patent
Crompton

(10) Patent No.: US 6,951,839 B1
(45) Date of Patent: Oct. 4, 2005

(54) METHODS AND COMPOSITIONS FOR REGULATING LYMPHOCYTE ACTIVITY

(75) Inventor: Tessa Crompton, London (GB)

(73) Assignee: Curis, Inc., Cambridge, MA (US)

(*) Notice: Subject to any disclaimer, the term of this patent is extended or adjusted under 35 U.S.C. 154(b) by 0 days.

(21) Appl. No.: 09/724,964

(22) Filed: Nov. 28, 2000

Related U.S. Application Data

(60) Provisional application No. 60/168,112, filed on Nov. 30, 1999.

(51) Int. Cl.[7] .......................... C07K 5/00; C07K 14/00; A61K 38/16; A01N 1/02; C12N 1/20
(52) U.S. Cl. .......................... 514/2; 530/300; 530/350; 530/388.22; 514/12; 436/501; 424/130.1; 424/198.1; 435/2; 435/69.5; 536/23.5
(58) Field of Search .................. 514/2, 12; 530/300, 530/350, 388.72; 436/501; 424/130.1, 198.1; 435/2, 695; 536/23.5

(56) References Cited

U.S. PATENT DOCUMENTS

| | | |
|---|---|---|
| 4,868,116 A | 9/1989 | Morgan et al. |
| 4,980,286 A | 12/1990 | Morgan et al. |
| 5,096,815 A | 3/1992 | Ladner et al. |
| 5,176,996 A | 1/1993 | Hogan et al. |
| 5,198,346 A | 3/1993 | Ladner et al. |
| 5,223,408 A | 6/1993 | Goeddel et al. |
| 5,223,409 A | 6/1993 | Ladner et al. |
| 5,256,775 A | 10/1993 | Froehler |
| 5,264,564 A | 11/1993 | Matteucci |
| 5,266,488 A | 11/1993 | Ordahl et al. |
| 5,286,654 A | 2/1994 | Cox et al. |
| 5,328,470 A | 7/1994 | Nabel et al. |

FOREIGN PATENT DOCUMENTS

| | | |
|---|---|---|
| WO | WO 88/06630 | 9/1988 |
| WO | WO 89/02468 | 3/1989 |
| WO | WO 89/05345 | 6/1989 |
| WO | WO 89/07136 | 8/1989 |
| WO | WO 90/02809 | 3/1990 |
| WO | WO 92/07573 | 5/1992 |
| WO | WO 92/09690 | 6/1992 |
| WO | WO 92/15679 | 9/1992 |
| WO | WO 93/09222 | 5/1993 |
| WO | WO 98/30520 A2 | 8/1993 |
| WO | WO 93/25234 | 12/1993 |
| WO | WO 95/18856 | 7/1995 |
| WO | WO 95/31560 | 11/1995 |
| WO | WO 96/17924 | 6/1996 |
| WO | WO 96/29411 | 9/1996 |
| WO | WO 00/74706 A1 | 12/2000 |
| WO | WO 02/080952 A2 | 10/2002 |

OTHER PUBLICATIONS

Bowie et al., 1990, Science 247:1306–1310.*
Alexander et al., Proc. Natl. Acad. Sci. 89(3352–3356) 1992.*
Lahana R., Drug Discovery Today, 4(10)447–448, 1999.*
Horrobin, DF, British Med. Journal, 322(7280)239, Jul. 2003.*
Stull and Iacovitti, Experimental Neurobiology 169(1)36–43, 2001.*
Lowery er al., J. Immunology 169(4)1869–75, 1999.*
Bubec et al., ALCOHOL 13(6)55–537, 1996.*
Bryce et al., Immunopharmacology 41(139–146)1999.*
Shah, D. et al. Reduced Thymocyte Development in Sonic Hedgehog Knockout Embryos, The Journal of Immunology. pp. 2296–2306 (2004).
Lin, J. et al. Increased cAMP and cAMP–Dependent Protein Kinase Activity Mediate Anti–CD2 Induced Suppression of Anti–CD3–Driven Interleukin–2 Production and CD25 Expression. Pathobiol. 63, 175–187 (1995).
Arkin and Yourvan, 1992, "An algorithm for protein engineering: simulations of recursive ensemble mutagenesis", Proc. Natl. Acad. Sci. USA 89:7811–7815.
Armentano et al., 1990, "Expression of human factor IX in rabbit hepatocytes by retrovirus–mediated gene transfer: potential for gene therapy of hemophillia B", Proc. Natl. Acad. Sci. USA 87:6141–6145.
Baldwin et al., 1984, "Cloning of the luciferase structural genes from *Vibrio harveyi* and expression of bioluminescence in *Escherichia coli*", Biochemistry 23:3663–3667.
Barbas et al., 1992, "Semisynthetic combinatorial antibody libraries: a chemical solution to the diversity problem", Proc. Natl. Acad. .Sci. USA 89:4457–4461.
Bass et al., 1990, "Hormone phage: an enrichment method for variant proteins with altered binding properties", Proteins 8:309–314.
Bear et al., 1992, "Purification and functional reconstitution of the cystic fibrosis transmembrane conductance regulator (CFTR)", Cell 68:809–818.
Ben–Bassat et al., 1987, "Processing of the initiation methionine from proteins: properties of the *Escherichia coli* methionine aminopeptidase and its gene structure", J. Bacteriol. 169:751–757.
Benoist et al., 1981, "In vivo sequence requirements of the SV40 early promotor region", Nature 290:304–310.
Berkner et al., 1988, "Development of adenovirus vectors for the expression of heterologous genes", Biotechniques 6:616–629.

(Continued)

Primary Examiner—Elizabeth C. Kemmerer
Assistant Examiner—Michael Brannock
(74) Attorney, Agent, or Firm—Ropes & Gray LLP

(57) ABSTRACT

The present application is directed to the discovery that hedgehog gene products, and signal transduction pathways involving hedgehog, are involved in maturation of T lymphocytes. Certain aspects of the invention are directed to preparations of hedgehog polypeptides, agonists, antagonists, or other molecules which regulate patched or smoothened signalling, and their uses as immunomodulatory agents.

15 Claims, 4 Drawing Sheets

OTHER PUBLICATIONS

Borle, 1990, "An overview of techniques for the measurement of calcium distribution, calcium fluxes, and cytosolic free calcium in mammalian cells", Environ. Health Perspect. 84:45–56.
Bumcrot et al., 1995, "Proteolytic processing yields two secreted forms of sonic hedgehog", Mol. Cell. Biol. 15:2294–2303.
Chang et al., 1994, "Products, genetic linkage and limb patterning activity of a murine hedgehog gene", Development 120:3339–3353.
Chen et al., "Gene therapy for brain tumors: regresssion of experimental gliomas by adenovirus–mediated gene transfer in vivo", Proc. Natl. Acad. Sci. USA 91:3054–3057.
Chowdhury et al. 1991, "Long–term improvement of hypercholesterolemia after ex vivo gene therapy in LDLR–deficient rabbits", Science 254:1802–1805.
Clackson et al., 1991, "Making antibody fragments using phage display libraries", Nature 352:624–628.
Cullen and Malim, 1992, "Secreted placental alkaline phosphatase as a eukaryotic reporter gene", Methods Enzymol. 216:362–368.
Cwirla et al., 1990, "Peptides on phage: a vast library of peptides for identifying ligands", Proc. Natl. Acad. Sci. USA 87:6378–6382.
Dai et al., 1992, "Gene therapy via primary myoblasts: long–term expression of factor IX protein following transplantation in vivo", Proc. Natl. Acad. Sci. USA 89:10892–10895.
Dann et al., 1986, "Human renin: a new class of inhibitors", Biochem. Biophys. Res. Commun. 134:71–77.
Danos and Mulligan, 1988, "Safe and efficient generation of recombinant retroviruses with amphotropic and ecotropic host ranges", Proc. Natl. Acad. Sci. USA 85:6460–6464.
Delgrave et al., 1993, "Recursive ensemble mutagenesis", Protein Eng. 6:327–331.
Dev et al., 1994, Electrochemotherapy—a novel method of cancer treatment, Cancer Treat. Rev. 20:105–115.
Devlin et al., 1990, "Random peptide libraries: a source of specific protein binding molecules", Science 249:404–406.
DeWet et al., 1987, "Firefly luciferase gene: structure and expression in mammalian cells", Mol. Cell Biol. 7:725–737.
Eglitis et al., 1985, "Gene expression in mice after high efficiency retroviral–mediated gene transfer", Science 230:1395–1398.
Ekker et al., 1995, "Patterning activities of vertebrate hedgehog proteins in the developing eye and brain", Curr. Biol. 5:944–955.
Ellison et al., 1991, "Epitope–tagged ubiquitin. A new probe for analyzing ubiquitin function", J. Biol. Chem. 266:21150–21157.
Ellman et al., 1958, "A colormetric method for determining low concentrations of mercaptans", Arch. Biochem. Biophys. 74:443.
Engebrecht and Silverman, 1984, "Identification of genes and gene products necessary for bacterial bioluminescence", Proc. Natl. Acad. Sci. USA 81:4154–4158.
Ettienne–Julan et al., 1992, "The efficiency of cell targeting by recombinant retroviruses depends on the nature of the receptor and the composition of the artificial cell–virus linker", J. Gen. Virol. 73 (Pt 12):3251–3255.
Ewenson et al., 1986, "Ketomethylene pseudopeptide analogues of substance P: synthesis and biological activity", J. Med. Chem. 29:295–299.
Ferry et al., 1991, "Retroviral–mediated gene transfer into hepatocytes in vivo", Proc. Natl. Acad. Sci. USA 88:8377–8381.
Fuchs et al., 1991, "Targeting recombinant antibodies to the surface of *Escherichia coli*: fusion to a petidoglycan associated lipoprotein", Bio/Technology 9:1370–1371.
Gallop et al., 1994, "Applications of combinatorial technologies to drug discovery. 1. Background and peptide combinatorial libraries", J. Med. Chem. 37:1233–1251.
Gordon et al., 1985, "Design of peptide derived amino alcohols as transition–state analog inhibitors of angiotensin converting enzyme", Biochem. Biophys. Res. Commun. 126:419–426.
Goud et al., 1983, "Antibody–mediated binding of a murine ecotropic Moloney retroviral vector to human cells allows internalization but not the establishment of the proviral state", Virology 163:251–254.
Goward et al, 1992, "Molecular evolution of bacterial cell-–surface proteins", Trends Biochem. Sci. 18:136–140 Rview.
Graham et al., 1991, "Manipulation of adenovirus vectors-"*Methods in Molecular Biology*(Humana, Clifton, NJ) vol. 7 pp. 109–127.
Griffiths et al., 1993, "Humans anti–self antibodies with high specificity from phage display libraries", EMBO J. 12:725–734.
Gunning et al., 1997, "A human beta–actin expression vector system directs high–level accumulation of antisense transcripts", Proc. Natl. Acad. Sci. USA 84:4831–4835.
Gustin et al., 1993, "Characterization of the role of individual protein binding motifs within the hepatitis B virus enhancer 1 on X promoter activity using linker scanning mutagenesis", Virology 193:653–660.
Habig et al., 1974, "Glutathione S–transferases. The first enzymatic step in mercapturic acid formation", J. Biol. Chem. 249:7130–7139.
Hahn et al., 1996, "Mutations of the human homolog of Drosophila patched in the nevoid basal cell carcinoma syndrome", Cell 85:841–851.
Haj–Ahmad et al., 1986, "Development of a helper–independent human adenovirus vector and its use in the transfer of the herpes simplex virus thymidine kinase gene", J. Virol. 57:267–274.
Hall et al., 1983, "Expression and regulation of *Escherichia coli* lacZ gene fusions in mammalian cells", J. Mol. Appl. Genet. 2:101–109.
Hammerschmidt et al., 1996, "Protein kinase A is a common negative regulator of Hedgehog signaling in the vertebrate embryo", Genes Dev. 10:647–658.
Hidalgo and Ingham, 1990, "Cell patterning in the Drosophila segment spatial regulation of the segment polarity gene patched", Development 110:291–301.
Hochuli et al., 1987, "New metal chelate adsorbent selective for proteins and peptides containing neighbouring histidine residues", J. Chromatogr. 411:177–184.
Huber et al., 1991, "Retroviral–mediated gene therapy for the treatment of hepatocellular carcinoma: an innovative approach for cancer therapy", Proc. Natl. Acad. Sci. USA 88:8039–8043.
Hui et al., 1994, "Expression of three mouse homologs of the Drosophila segment polarity gene cubitus interruptus, Gli, Gli–2, and Gli–3, in ectoderm– and mesoderm–derived tissues suggests multiple roles during postimplantation development", Dev. Biol. 162:402–413.

Huston et al., 1988, "Protein engineering of antibody binding sites: recovery of specific activity in an anti–digoxin single–chain Fv analogue produced in *Escherichia coli*", Proc. Natl. Acad. Sci. USA 85:5879–5883.

Hwu et al., 1993, "Functional and molecular characterization of tumor–infiltrating lymphocytes transduced with tumor necrosis factor–alpha cDNA for the gene therapy of cancer in humans", J. Immunol. 150:4104–4115.

Hynes, 1987, "Integrins: a family of cell surface receptors", Cell 48:549–554.

Hynes, 1992, "Integrins: versatility, modulation, and signaling in cell adhesion", Cell 69:11–25.

Ike et al., 1983, "Solid phase synthesis of polynucleotides. VIII. Synthesis of mixed oligodeoxyribonucleotides by the phosphotriester solid phase method", Nucleic Acids Res. 11:477–488.

Itakura et al., 1981, Recombinant DNA, Proc. 3$^{rd}$ Cleveland Symposium On Macromolecules, A.G. Walton, ed. (Elsevier, Amsterdam) pp. 273–289.

Itakura et al., 1984, "Expression in *Escherichia coli* of a chemically synthesized gene for the hormone somatostatin", Science 1998:1056–1063.

Itakura et al., 1984, "Synthesis and use of synthetic oligonucleotides", Annu. Rev. Biochem. 53:323–356.

Johnson et al., 1996, "Human homolog of patched, a candidate gene for the basal cell nevus syndrome", Science 272:1668–1671.

Jones et al., 1979, "Isolation of adenovirus type 5 host range deletion mutants defective for transformation of rat embryo cells", Cell 17:683–689.

Karasuyama et al., 1989, "Autocrine growth and tumorigenicity of interleukin 2–dependent helper T cells transfected with IL–2 gene", J. Exp. Med. 169:13–25.

Kay et al., 1992, "Hepatic gene therapy: persistent expression of human alpha 1–antitrypsin in mice after direct gene delivery in vivo", Hum. Gene Ther. 3:641–647.

Kinzler et al., 1990, "The GLI gene encodes a nuclear protein which binds specific sequences in the human genome", Mol. Cell. Biol. 10:634–642.

Klessig et al., 1984, "Introduction, stable integration, and controlled expression of a chimeric adenovirus gene whose product is toxic to the recipient human cell", Mol. Cell. Biol. 4:1354–1362.

Kornblihtt et al., 1985, "Primary structure of human fibronectin: differential splicing may generate at least 10 polypeptides from a single gene", EMBO J. 4:1755–1759.

Kube et al., 1995, "Isolation of the human interleukin 10 promoter. Characterization of the promoter activity in Burkitt's lymphoma cell lines", Cytokine 7:1–7.

Lai et al., 1995, "Patterning of the ectoderm of Xenopus laevis by the amino–terminal product of hedgehog autoproteolytic cleavage", Development 121:2349–2360.

Lee et al., 1992, "Secretion and localized transcription suggest a role in positional signaling for products of the segmentation gene hedgehog", Cell 71:33–50.

Lee et al., 1994, "Autoproteolysis in hedgehog protein biogenesis", Science 266:1528–1537.

Lyons and Nelson, 1984, "An immunological method for detecting gene expression in yeast colonies", Proc. Natl. Acad. Sci. USA 81:7426–7430.

Marigo and Tabin, 1996, "Regulation of patched by sonic hedgehog in the developing neural tube", Proc. Natl. Acad. Sci. USA 93:9346–9351.

Marigo et al., 1996, "Conservation in hegdehog signaling: induction of a chicken patched homolog by Sonic hedgehog in the developing limb", Development 122:1225–1233.

Marks et al., 1992, "Molecular evolution of proteins on filamentous phage. Mimicking the strategy of the immune system", J. Biol. Chem. 267:16007–16010.

Marti et al., 1995, "Distribution of Sonic hedgehog peptides in the developing chick and mouse embryo", Development 121:2537–2547.

Miller et al., 1987, "N–terminal methionine–specific peptidase in *Salmonella typhimurium*", Proc. Natl. Acad. Sci. USA 84:2718–2722.

Miller, 1990, "Progress toward human gene therapy", Blood 76:271–178.

Narang, 1983, "DNA synthesis", Tetrahedron 39:3–22.

Neda et al., 1991, "Chemical modification of an ecotropic murine leukemia virus results in redirection of its target cell specificity", J. Biol. Chem. 266:14143–14146.

Newton et al., 1983, "Transfer of band 3, the erythrocyte anion transporter, between phospolipid vesicles and cells", Biochemistry 22:6110–6117.

Orenic et al., 1996, "Cloning and characterization of the segment polarity gene cubitus interruptus Dominant of Drosophila", Genes Dev. 4:1053–1067.

Partis et al., 1983, "Cross–linking of protein by ω–maleimido alkanoyl n–hydroxysuccinimido esters", J. Pro. Chem. 2:263.

Pepinsky et al., 1998, "Identification of a palmitic acid–modified form of human Sonic hedgehog", J. Biol. Chem. 273:14037–14045.

Pierschbacher et al., 1984, "Cell attachment activity of fibronetin can be duplicated by small synthetic fragments of the molecule", Nature 309:30–33.

Pierschbacher et al., 1987, "Influence of stereochemistry of the sequence Arg–Gly–Asp–Xaa on binding specificity in cell adhesion", J. Biol. Chem. 262:17294–17298.

Porter et al., 1995, "The product of hedgehog autoproteolytic cleavage active in local and long–range signalling", Nature 374:363–366.

Porter et al., 1996, "Hedgehog patterning activity: role of a lipophilic modification mediated by the carboxy–terminal autoprocessing domain", Cell 86:21–34.

Preat et al., 1990, "A putative serine/threonine protein kinase encoded by the segment–polarity fused gene of Drosophila", Nature 347:87–89.

Reber et al., 1987, "Hydrophobic properties of the beta 1 and beta 2 subunits of the rat brain sodium channel", J. Biol. Chem. 262:11369–11374.

Riddles et al., 1979, "Ellman's reagent: 5,5'–dithiobis(2–nitrobenzoic acid)—a reexamination", Anal. Biochem. 94:75–81.

Roberts et al., 1992, "Directed evolution of a protein: selection of potent neutrophil elastase inhibitors displayed on M13 fusion phage", Proc. Natl. Acad. Sci. USA 89:2429–2433.

Roelink et al., 1995, "Floor plate and motor neuron induction by different concentrations of the amino–terminal cleavage product of sonic hedgehog autoproteolysis", Cell 81:445–455.

Roman et al., 1994, "Mapping of Hap 70–binding sites on protein antigens", Eur. J. Biochem. 222:65–73.

Rosenfeld et al., 1991, "Adenovirus–mediated transfer of a recombinant alpha 1–antitrypsin gene to the lung epithelium in vivo", Science 252:431–434.

Rosenfeld et al., 1992, "In vivo transfer of the human cystic fibrosis transmembrane conductance regulator gene to the airway epithelium", Cell 68:143–155.

Roux et al., 1989, "A versatile and potentially general approach to the targeting of specific cell types by retroviruses: application to the infection of human cells by means of major histocompatibility complex class I and class II antigens by mouse ecotropic murine leukemia virus–derived viruses", Proc. Natl. Acad. Sci. USA ;86:9079–9083.

Ruoslahti et al., 1987, "New perspectives in cell adhesion: RGD and integrins", Science 238:491–497.

Sato et al., 1986, "Synthesis and antibiotic activity of a gramicidin s analogue containing bicyclic beta–turn dipeptides", J. Chem. Soc. Perkin Trans. 1:1231.

Sato et al., 1995, "Structure and regulation of the gene encoding the neuron–specific porotein kinase C substrate neurogranin (RC3 protein)", J. Biol. Chem. 270:10314–10322.

Scott et al., 1990, "Searching for peptide ligands with an epitope library", Science 249:386–390.

Sprague et al., 1983, "Expression of a recombinant DNA gene coding for the vesicular stomatits virus nucleocapsid protein", J. Virol. 45:773–781.

Stein et al., 1988, Oligodeoxynucleotides as inhibitors of gene expression: a review, Cancer Res. 48:2659–2668 Review.

Tabata et al., 1992, "The Drosophila hedgehog gene is expressed specifically in posterior compartment cells and is a target of engrailed regulation", Genes Dev. 6:2635–2645.

Templeton et al., 1984, "N–terminal amino acid sequences of the polyoma middle–size T antigen are important for protein kinase activity and cell transformation", Mol. Cel. Biol. 4:817–821.

Therond et al., 1993, "Molecular organisation and expression pattern of the segment polarity gene fused of *Drosophila melanogaster*", Mech. Dev. 44:65–80.

Toh et al., 1989, "Isolation and characterization of a rat liver alkaline phosphatase gene. A single gene with two promoters", Eur. J. Biochem. 182:231–237.

* cited by examiner

SEQUENCE LISTING

<160> NUMBER OF SEQ ID NOS: 28

<210> SEQ ID NO 1
<211> LENGTH: 1277
<212> TYPE: DNA
<213> ORGANISM: Gallus gallus

<400> SEQUENCE: 1

| | | | | | |
|---|---|---|---|---|---|
| atggtcgaaa | tgctgctgtt | gacaagaatt | ctcttggtgg | gcttcatctg cgctctttta | 60 |
| gtctcctctg | ggctgacttg | tggaccaggc | agggcattg | gaaaaggag gcaccccaaa | 120 |
| aagctgaccc | cgttagccta | taagcagttt | attcccaatg | tggcagagaa gaccctaggg | 180 |
| gccagtggaa | gatatgaagg | gaagatcaca | agaaactccg | agagatttaa agaactaacc | 240 |
| ccaaattaca | accctgacat | tatttttaag | gatgaagaga | cacgggagc tgacagactg | 300 |
| atgactcagc | gctgcaagga | caagctgaat | gccctggcga | tctcggtgat gaaccagtgg | 360 |
| cccggggtga | agctgcgggt | gaccgagggc | tgggacgagg | atggccatca ctccgaggaa | 420 |
| tcgctgcact | acgagggtcg | cgccgtggac | atcaccacgt | cggatcggga ccgcagcaag | 480 |
| tacggaatgc | tggcccgcct | cgccgtcgag | gccggcttcg | actgggtcta ctacgagtcc | 540 |
| aaggcgcaca | tccactgctc | cgtcaaagca | gaaaactcag | tggcagcgaa atcaggaggc | 600 |
| tgcttccctg | gctcagccac | agtgcacctg | gagcatggag | gcaccaagct ggtgaaggac | 660 |
| ctgagccctg | ggaccgcgt | gctggctgct | gacgcggacg | gccggctgct ctacagtgac | 720 |
| ttcctcacct | tcctcgaccg | gatggacagc | tcccgaaagc | tcttctacgt catcgagacg | 780 |
| cggcagcccc | gggcccggct | gctactgacg | gcggcccacc | tgctcttgt ggccccccag | 840 |
| cacaaccagt | cggaggccac | aggtccacc | agtggccagg | cgctcttcgc cagcaacgtg | 900 |
| aagcctggcc | aacgtgtcta | tgtgctgggc | gagggcggc | agcagctgct gccggcgtct | 960 |
| gtccacagcg | tctcattgcg | ggaggaggcg | tccggagcct | acgcccact caccgcccag | 1020 |
| ggcaccatcc | tcatcaaccg | ggtgttggc | tcctgctacg | ccgtcatcga ggagcacagt | 1080 |
| tgggcccatt | gggccttcgc | accattccgc | ttggctcagg | gctgctggc cgccctctgc | 1140 |
| ccagatgggg | ccatccctac | tgccgccacc | accaccactg | gcatccattg gtactcacgg | 1200 |
| ctcctctacc | gcatcggcag | ctgggtgctg | gatggtgacg | cgctgcatcc gctgggcatg | 1260 |
| gtggcaccgg | ccagctg | | | | 1277 |

<210> SEQ ID NO 2
<211> LENGTH: 1190
<212> TYPE: DNA
<213> ORGANISM: Mus musculus

<400> SEQUENCE: 2

| | | | | | |
|---|---|---|---|---|---|
| atggctctgc | cggccagtct | gttgcccctg | tgctgcttgg | cactcttggc actatctgcc | 60 |
| cagagctgcg | ggccgggccg | aggaccggtt | ggccggcggc | gttatgtgcg caagcaactt | 120 |
| gtgcctctgc | tatacaagca | gtttgtgccc | agtatgcccg | agcggaccct gggcgcgagt | 180 |
| gggccagcgg | aggggagggt | aacaagggg | tcggagcgct | tccgggacct cgtacccaac | 240 |
| tacaaccccg | acataatctt | caaggatgag | gagaacagcg | cgcagaccg cctgatgaca | 300 |
| gagcgttgca | aagagcgggt | gaacgctcta | gccatcgcgg | tgatgaacat gtggcccgga | 360 |
| gtacgcctac | gtgtgactga | aggctgggac | gaggacggcc | accacgcaca ggattcactc | 420 |
| cactacgaag | gccgtgcctt | ggacatcacc | acgtctgacc | gtgaccgtaa taagtatggt | 480 |

-continued

```
ttgttggcgc gcctagctgt ggaagccgga ttcgactggg tctactacga gtcccgcaac      540
cacatccacg tatcggtcaa agctgataac tcactggcgg tccgagccgg aggctgcttt      600
ccgggaaatg ccacggtgcg cttgcggagc ggcgaacgga aggggctgag ggaactacat      660
cgtggtgact gggtactggc cgctgatgca gcgggccgag tggtacccac gccagtgctg      720
ctcttcctgg accgggatct gcagcgccgc gcctcgttcg tggctgtgga gaccgagcgg      780
cctccgcgca aactgttgct cacaccctgg catctggtgt tcgctgctcg cgggccagcg      840
cctgctccag gtgactttgc accggtgttc gcgcgccgct acgtgctggc cgactcggtg      900
ctggctcccg gcggggacgc gctccagccg gcgcgcgtag cccgcgtggc gcgcgaggaa      960
gccgtgggcg tgttcgcacc gctcactgcg cacgggacgc tgctggtcaa cgacgtcctc     1020
gcctcctgct acgcggttct agagagtcac cagtgggccc accgcgcctt cgccccttg      1080
cggctgctgc acgcgctcgg ggctctgctc cctgggggtg cagtccagcc gactggcatg     1140
cattggtact ctcgcctcct ttaccgcttg gccgaggagt aatgggctg                 1190
```

<210> SEQ ID NO 3
<211> LENGTH: 1281
<212> TYPE: DNA
<213> ORGANISM: Mus musculus

<400> SEQUENCE: 3

```
atgtctcccg cctggctccg gccccgactg cggttctgtc tgttcctgct gctgctgctt       60
ctggtgccgg cggcgggg ctgcgggccg ggccgggtgg tgggcagccg ccggaggccg         120
cctcgcaagc tcgtgcctct tgcctacaag cagttcagcc ccaacgtgcc ggagaagacc      180
ctgggcgcca gcggcgcta cgaaggcaag atcgcgcgca gctctgagcg cttcaaagag       240
ctcacccca actacaatcc cgacatcatc ttcaaggacg aggagaacac gggtgccgac       300
cgcctcatga cccagcgctg caaggaccgt ctgaactcac tggccatctc tgtcatgaac      360
cagtggcctg gtgtgaaact gcgggtgacc gaaggccggg atgaagatgg ccatcactca     420
gaggagtctt tacactatga gggccgcgcg gtggatatca ccacctcaga ccgtgaccga      480
aataagtatg gactgctggc gcgcttagca gtggaggccg gcttcgactg ggtgtattac      540
gagtccaagg cccacgtgca ttgctctgtc aagtctgagc attcggccgc tgccaagaca      600
ggtggctgct ttcctgccgg agcccaggtg cgcctagaga acggggagcg tgtggccctg      660
tcagctgtaa agccaggaga ccgggtgctg gccatggggg aggatgggac ccccaccttc      720
agtgatgtgc ttattttcct ggaccgcgag ccaaaccggc tgagagcttt ccaggtcatc      780
gagactcagg atcctccgcg tcggctggcg ctcacgcctg cccacctgct cttcattgcg      840
gacaatcata cagaaccagc agcccacttc cgggccacat ttgccagcca tgtgcaacca      900
ggccaatatg tgctggtatc aggggtacca ggcctccagc ctgctcgggt ggcagctgtc      960
tccacccacg tggcccttgg gtcctatgct cctctcacaa ggcatgggac acttgtggtg     1020
gaggatgtgg tggcctcctg cttttgcagct gtggctgacc accatctggc tcagttggcc    1080
ttctggcccc tgcgactgtt tcccagtttg gcatgggca gctggacccc aagtgagggt      1140
gttcactcct accctcagat gctctaccgc ctggggcgtc tcttgctaga agagagcacc     1200
ttccatccac tgggcatgtc tggggcagga agctgaaggg actctaacca ctgccctcct     1260
ggaactgctg tgcgtggatc c                                               1281
```

<210> SEQ ID NO 4

<211> LENGTH: 1313
<212> TYPE: DNA
<213> ORGANISM: Mus musculus

<400> SEQUENCE: 4

| | | | | | |
|---|---|---|---|---|---|
| atgctgctgc | tgctggccag | atgttttctg | gtgatccttg | cttcctcgct | gctggtgtgc | 60 |
| cccgggctgg | cctgtgggcc | cggcagggggg | tttggaaaga | ggcggcaccc | caaaaagctg | 120 |
| accccttag | cctacaagca | gtttattccc | aacgtagccg | agaagaccct | aggggccagc | 180 |
| ggcagatatg | aagggaagat | cacaagaaac | tccgaacgat | ttaaggaact | caccccaat | 240 |
| tacaaccccg | acatcatatt | taaggatgag | gaaaacacgg | gagcagaccg | gctgatgact | 300 |
| cagaggtgca | agacaagtt | aaatgccttg | gccatctctg | tgatgaacca | gtggcctgga | 360 |
| gtgaggctgc | gagtgaccga | gggctgggat | gaggacggcc | atcattcaga | ggagtctcta | 420 |
| cactatgagg | gtcgagcagt | ggacatcacc | acgtccgacc | gggaccgcag | caagtacggc | 480 |
| atgctggctc | gcctggctgt | ggaagcaggt | ttcgactggg | tctactatga | atccaaagct | 540 |
| cacatccact | gttctgtgaa | agcagagaac | tccgtggcgg | ccaaatccgg | cggctgtttc | 600 |
| ccgggatccg | ccaccgtgca | cctggagcag | ggcggcacca | gctggtgaa | ggacttacgt | 660 |
| cccggagacc | gcgtgctggc | ggctgacgac | cagggccggc | tgctgtacag | cgacttcctc | 720 |
| accttcctgg | accgcgacga | aggcgccaag | aaggtcttct | acgtgatcga | gacgctggag | 780 |
| ccgcgcgagc | gcctgctgct | caccgccgcg | cacctgctct | tcgtggcgcc | gcacaacgac | 840 |
| tcggggccca | cgcccgggcc | aagcgcgctc | tttgccagcc | gcgtgcgccc | cgggcagcgc | 900 |
| gtgtacgtgg | tggctgaacg | cggcggggac | cgccggctgc | tgcccgccgc | ggtgcacagc | 960 |
| gtgacgctgc | gagaggagga | ggcgggcgcg | tacgcgccgc | tcacggcgca | cggcaccatt | 1020 |
| ctcatcaacc | gggtgctcgc | ctcgtgctac | gctgtcatcg | aggagcacag | ctgggcacac | 1080 |
| cgggccttcg | cgccttttccg | cctggcgcac | gcgctgctgg | ccgcgctggc | acccgcccgc | 1140 |
| acggacggcg | ggggcggggg | cagcatccct | gcagcgcaat | ctgcaacgga | agcgaggggc | 1200 |
| gcggagccga | ctgcgggcat | ccactggtac | tcgcagctgc | tctaccacat | tggcacctgg | 1260 |
| ctgttggaca | gcgagaccat | gcatcccttg | ggaatggcgg | tcaagtccag | ctg | 1313 |

<210> SEQ ID NO 5
<211> LENGTH: 1256
<212> TYPE: DNA
<213> ORGANISM: Brachydanio rerio

<400> SEQUENCE: 5

| | | | | | |
|---|---|---|---|---|---|
| atgcggcttt | tgacgagagt | gctgctggtg | tctcttctca | ctctgtcctt | ggtggtgtcc | 60 |
| ggactggcct | gcggtcctgg | cagaggctac | ggcagaagaa | gacatccgaa | gaagctgaca | 120 |
| cctctcgcct | acaagcagtt | catacctaat | gtcgcggaga | agaccttagg | ggccagcggc | 180 |
| agatacgagg | gcaagataac | gcgcaattcg | gagagattta | agaacttac | tccaaattac | 240 |
| aatcccgaca | ttatctttaa | ggatgaggag | aacacgggag | cggacaggct | catgacacag | 300 |
| agatgcaaag | acaagctgaa | ctcgctggcc | atctctgtaa | tgaaccactg | gccagggggtt | 360 |
| aagctgcgtg | tgacagaggg | ctgggatgag | gacggtcacc | attttgaaga | atcactccac | 420 |
| tacgagggaa | gagctgttga | tattaccacc | tctgaccgag | acaagagcaa | atacgggaca | 480 |
| ctgtctcgcc | tagctgtgga | ggctggattt | gactgggtct | attacgagtc | caaagcccac | 540 |
| attcattgct | ctgtcaaagc | agaaaattcg | gttgctgcga | atctgggggg | ctgtttccca | 600 |
| ggttcggctc | tggtctcgct | ccaggacgga | ggacagaagg | ccgtgaagga | cctgaaccc | 660 |

-continued

```
ggagacaagg tgctggcggc agacagcgcg ggaaacctgg tgttcagcga cttcatcatg      720
ttcacagacc gagactccac gacgcgacgt gtgttttacg tcatagaaac gcaagaaccc      780
gttgaaaaga tcaccctcac cgccgctcac ctccttttg tcctcgacaa ctcaacggaa       840
gatctccaca ccatgaccgc cgcgtatgcc agcagtgtca gagccggaca aaaggtgatg      900
gttgttgatg atagcggtca gcttaaatct gtcatcgtgc agcggatata cacgaggag       960 cagcggggct cgttcgcacc agtgactgca catgggacca ttgtggtcga cagaatactg     1020
gcgtcctgtt acgccgtaat agaggaccag gggcttgcgc atttggcctt cgcgcccgcc     1080
aggctctatt attacgtgtc atcattcctg tcccccaaaa ctccagcagt cggtccaatg     1140
cgactttaca acaggagggg gtccactggt actccaggct cctgtcatca aatgggaacg     1200
tggcttttgg acagcaacat gcttcatcct ttggggatgt cagtaaactc aagctg         1256
```

<210> SEQ ID NO 6
<211> LENGTH: 1425
<212> TYPE: DNA
<213> ORGANISM: Homo sapiens
<220> FEATURE:
<221> NAME/KEY: modified_base
<222> LOCATION: (1387...1389)
<223> OTHER INFORMATION: n=a, c, g, or t

<400> SEQUENCE: 6

```
atgctgctgc tggcgagatg tctgctgcta gtcctcgtct cctcgctgct ggtatgctcg       60
ggactggcgt gcggaccggg caggggttc gggaagagga ggcaccccaa aaagctgacc       120
cctttagcct acaagcagtt tatccccaat gtggccgaga agaccctagg cgccagcgga      180
aggtatgaag gaagatctc cagaaactcc gagcgattta aggaactcac ccccaattac       240
aaccccgaca tcatatttaa ggatgaagaa acaccggag cggacaggct gatgactcag       300
aggtgtaagg acaagttgaa cgctttggcc atctcggtga tgaaccagtg gccaggagtg      360
aaactgcggg tgaccgaggg ctgggacgaa gatggccacc actcagagga gtctctgcac      420
tacgagggcc gcgcagtgga catcaccacg tctgaccgcg accgcagcaa gtacggcatg      480
ctggcccgcc tggcggtgga ggccggcttc gactgggtgt actacgagtc caaggcacat      540
atccactgct cggtgaaagc agagaactcg gtggcggcca atcgggagg ctgcttcccg       600 ggctcggcca cggtgcacct ggagcagggc ggcaccaagc tggtgaagga cctgagcccc      660
ggggaccgcg tgctggcggc ggacgaccag ggccggctgc tctacagcga cttcctcact     720
ttcctggacc gcgacgacgg cgccaagaag gtcttctacg tgatcgagac gcgggagccg      780 cgcgagcgc tgctgctcac cgccgcgcac ctgctctttg tggcgccgca caacgactcg      840
gccaccgggg agcccgaggc gtcctcgggc tcggggccgc cttccggggg cgcactgggg      900
cctcgggcgc tgttcgccag ccgcgtgcgc ccgggccagc gcgtgtacgt ggtggccgag      960
cgtgacgggg accgccggct cctgcccgcc gctgtgcaca gcgtgaccct aagcgaggag     1020
gccgcgggcg cctacgcgcc gctcacggcc cagggcacca ttctcatcaa ccgggtgctg     1080
gcctcgtgct acgcggtcat cgaggagcac agctgggcgc accgggcctt cgcgcccttc     1140
cgcctggcgc acgcgctcct ggctgcactg gcgcccgcgc gcacggaccg cggcggggac     1200
agcggcggcg gggaccgcgg gggcggcggc ggcagagtag ccctaaccgc tccaggtgct     1260
gccgacgctc cggtgcgggg ggccaccgcg ggcatccact ggtactcgca gctgctctac     1320
caaataggca cctggctcct ggacagcgag gccctgcacc cgctgggcat ggcggtcaag     1380
```

| | |
|---|---|
| tccagcnnna gccgggggc cggggagg gcgcgggagg gggcc | 1425 |

<210> SEQ ID NO 7
<211> LENGTH: 1622
<212> TYPE: DNA
<213> ORGANISM: Homo sapiens

<400> SEQUENCE: 7

| | |
|---|---|
| catcagccca ccaggagacc tcgcccgccg ctccccggg ctccccggcc atgtctcccg | 60 |
| cccggctccg gccccgactg cacttctgcc tggtcctgtt gctgctgctg gtggtgcccg | 120 |
| cggcatgggg ctgcgggccg ggtcgggtgg tgggcagccg ccggcgaccg ccacgcaaac | 180 |
| tcgtgccgct cgcctacaag cagttcagcc ccaatgtgcc cgagaagacc ctgggcgcca | 240 |
| gcggacgcta tgaaggcaag atcgctcgca gctccgagcg cttcaaggag ctcacccca | 300 |
| attacaatcc agacatcatc ttcaaggacg aggagaacac aggcgccgac cgcctcatga | 360 |
| cccagcgctg caaggaccgc ctgaactcgc tggctatctc ggtgatgaac cagtggcccg | 420 |
| gtgtgaagct gcgggtgacc gagggctggg acgaggacgg ccaccactca gaggagtccc | 480 |
| tgcattatga gggccgcgcg gtggacatca ccacatcaga ccgcgaccgc aataagtatg | 540 |
| gactgctggc gcgcttggca gtggaggccg gctttgactg ggtgtattac gagtcaaagg | 600 |
| cccacgtgca ttgctccgtc aagtccgagc actcggccgc agccaagacg ggcggctgct | 660 |
| tccctgccgg agcccaggta cgcctggaga gtggggcgcg tgtggccttg tcagccgtga | 720 |
| ggccgggaga ccgtgtgctg gccatggggg aggatgggag ccccaccttc agcgatgtgc | 780 |
| tcattttcct ggaccgcgag ccccacaggc tgagagcctt ccaggtcatc gagactcagg | 840 |
| accccccacg ccgcctggca ctcacacccg ctcacctgct ctttacggct gacaatcaca | 900 |
| cggagccggc agcccgcttc cgggccacat ttgccagcca cgtgcagcct ggccagtacg | 960 |
| tgctggtggc tggggtgcca ggcctgcagc ctgcccgcgt ggcagctgtc tctacacacg | 1020 |
| tggccctcgg ggcctacgcc ccgctcacaa gcatgggac actggtggtg gaggatgtgg | 1080 |
| tggcatcctg cttcgcggcc gtggctgacc accacctggc tcagttggcc ttctggcccc | 1140 |
| tgagactctt tcacagcttg gcatggggca gctggacccc ggggagggt gtgcattggt | 1200 |
| accccagct gctctaccgc ctgggcgtc tcctgctaga agagggcagc ttccacccac | 1260 |
| tgggcatgtc cggggcaggg agctgaaagg actccaccgc tgccctcctg gaactgctgt | 1320 |
| actgggtcca gaagcctctc agccaggagg gagctggccc tggaagggac ctgagctggg | 1380 |
| ggacactggc tcctgccatc tcctctgcca tgaagataca ccattgagac ttgactgggc | 1440 |
| aacaccagcg tcccccaccc gcgtcgtggt gtagtcatag agctgcaagc tgagctggcg | 1500 |
| aggggatggt tgttgacccc tctctcctag agaccttgag gctggcacgg cgactcccaa | 1560 |
| ctcagcctgc tctcactacg agttttcata ctctgcctcc cccattggga gggcccattc | 1620 |
| cc | 1622 |

<210> SEQ ID NO 8
<211> LENGTH: 1191
<212> TYPE: DNA
<213> ORGANISM: Homo sapiens

<400> SEQUENCE: 8

| | |
|---|---|
| atggctctcc tgaccaatct actgcccttg tgctgcttgg cacttctggc gctgccagcc | 60 |
| cagagctgcg gccgggccg ggggccggtt ggccggcgcc gctatgcgcg caagcagctc | 120 |
| gtgccgctac tctacaagca atttgtgccc ggcgtgccag agcggaccct gggcgccagt | 180 |

-continued

```
gggccagcgg aggggagggt ggcaaggggc tccgagcgct tccgggacct cgtgcccaac      240
tacaaccccg acatcatctt caaggatgag agaacagtg gagccgaccg cctgatgacc       300
gagcgttgca aggagagggt gaacgctttg gccattgccg tgatgaacat gtggcccgga     360
gtgcgcctac gagtgactga gggctgggac gaggacggcc accacgctca ggattcactc     420
cactacgaag gccgtgcttt ggacatcact acgtctgacc gcgaccgcaa caagtatggg     480
ttgctggcgc gcctcgcagt ggaagccggc ttcgactggg tctactacga gtcccgcaac     540
cacgtccacg tgtcggtcaa agctgataac tcactggcgg tccgggcggg cggctgcttt     600
ccgggaaatg caactgtgcg cctgtggagc ggcgagcgga aagggctgcg ggaactgcac     660
cgcggagact gggttttggc ggccgatgcg tcaggccggg tggtgcccac gccggtgctg     720
ctcttcctgg accgggactt gcagcgccgg gcttcatttg tggctgtgga gaccgagtgg     780
cctccacgca aactgttgct cacgccctgg cacctggtgt ttgccgctcg agggccggcg     840
cccgcgccag gcgactttgc accggtgttc gcgcgccggc tacgcgctgg ggactcggtg    900
ctggcgcccg gcggggatgc gcttcggcca gcgcgcgtgg cccgtgtggc gcgggaggaa     960
gccgtgggcg tgttcgcgcc gctcaccgcg cacgggacgc tgctggtgaa cgatgtcctg    1020
gcctcttgct acgcggttct ggagagtcac cagtgggcgc accgcgcttt tgccccccttg   1080 agactgctgc acgcgctagg ggcgctgctc cccgcgggg ccgtccagcc gactggcatg     1140
cattggtact ctcggctcct ctaccgctta gcggaggagc tactgggctg a              1191
```

<210> SEQ ID NO 9
<211> LENGTH: 1251
<212> TYPE: DNA
<213> ORGANISM: Brachydanio rerio

<400> SEQUENCE: 9

```
atggacgtaa ggctgcatct gaagcaattt gctttactgt gttttatcag cttgcttctg      60
acgccttgtg gattagcctg tggtcctggt agaggttatg gaaaacgaag acacccaaag    120
aaattaaccc cgttggctta caagcaattc atccccaacg ttgctgagaa acgcttggaa    180
gccagcggca aatacgaagg caaaatcaca aggaattcag agagatttaa agagctgatt    240
ccgaattata atccccgatat catctttaag gacgaggaaa acacaaacgc tgacaggctg    300
atgaccaagc gctgtaagga caagttaaat tcgttggcca tatccgtcat gaaccactgg    360
cccggcgtga aactgcgcgt cactgaaggc tgggatgagg atggtcacca tttagaagaa    420
tctttgcact atgagggacg ggcagtggac atcactacct cagacaggga taaaagcaag    480
tatgggatgc tatccaggct tgcagtggag gcaggattcg actgggtcta ttatgaatct    540
aaagcccaca tacactgctc tgtcaaagca gaaaattcag tggctgctaa atcaggagga    600
tgttttcctg ggtctgggac ggtgacactt ggtgatggga cgaggaaacc catcaaagat    660
cttaaagtgg gcgaccgggt tttggctgca gacgagaagg gaaatgtctt aataagcgac    720
tttattatgt ttatagacca cgatccgaca acgagaaggc aattcatcgt catcgagacg    780
tcagaacctt tcaccaagct cacctcact gccgcgcacc tagttttcgt tggaaactct    840
tcagcagctt cgggtataac agcaacattt gccagcaacg tgaagcctgg agatacagtt    900
ttagtgtggg aagacacatg cgagagcctc aagagcgtta cagtgaaaag gatttacact    960
gaggagcacg agggctcttt tgcgccagtc accgcgcacg gaaccataat agtggatcag    1020
gtgttggcat cgtgctacgc ggtcattgag aaccacaaat gggcacattg ggcttttgcg    1080
```

-continued

```
ccggtcaggt tgtgtcacaa gctgatgacg tggcttttc cggctcgtga atcaaacgtc    1140
aattttcagg aggatggtat ccactggtac tcaaatatgc tgtttcacat cggctcttgg    1200
ctgctggaca gagactcttt ccatccactc gggattttac acttaagttg a             1251
```

<210> SEQ ID NO 10
<211> LENGTH: 425
<212> TYPE: PRT
<213> ORGANISM: Gallus gallus

<400> SEQUENCE: 10

```
Met Val Glu Met Leu Leu Leu Thr Arg Ile Leu Leu Val Gly Phe Ile
 1               5                  10                  15

Cys Ala Leu Leu Val Ser Ser Gly Leu Thr Cys Gly Pro Gly Arg Gly
             20                  25                  30

Ile Gly Lys Arg Arg His Pro Lys Lys Leu Thr Pro Leu Ala Tyr Lys
         35                  40                  45

Gln Phe Ile Pro Asn Val Ala Glu Lys Thr Leu Gly Ala Ser Gly Arg
     50                  55                  60

Tyr Glu Gly Lys Ile Thr Arg Asn Ser Glu Arg Phe Lys Glu Leu Thr
 65                  70                  75                  80

Pro Asn Tyr Asn Pro Asp Ile Ile Phe Lys Asp Glu Asn Thr Gly
                 85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
    130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Thr Ala Ala
            260                 265                 270

His Leu Leu Phe Val Ala Pro Gln His Asn Gln Ser Glu Ala Thr Gly
        275                 280                 285

Ser Thr Ser Gly Gln Ala Leu Phe Ala Ser Asn Val Lys Pro Gly Gln
    290                 295                 300

Arg Val Tyr Val Leu Gly Glu Gly Gly Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350
```

-continued

Tyr Ala Val Ile Glu Glu His Ser Trp Ala His Trp Ala Phe Ala Pro
            355                 360                 365

Phe Arg Leu Ala Gln Gly Leu Leu Ala Ala Leu Cys Pro Asp Gly Ala
        370                 375                 380

Ile Pro Thr Ala Ala Thr Thr Thr Gly Ile His Trp Tyr Ser Arg
385                 390                 395                 400

Leu Leu Tyr Arg Ile Gly Ser Trp Val Leu Asp Gly Asp Ala Leu His
                405                 410                 415

Pro Leu Gly Met Val Ala Pro Ala Ser
            420                 425

<210> SEQ ID NO 11
<211> LENGTH: 396
<212> TYPE: PRT
<213> ORGANISM: Mus musculus

<400> SEQUENCE: 11

Met Ala Leu Pro Ala Ser Leu Pro Leu Cys Cys Leu Ala Leu Leu
1               5                   10                  15

Ala Leu Ser Ala Gln Ser Cys Gly Pro Gly Arg Gly Pro Val Gly Arg
            20                  25                  30

Arg Arg Tyr Val Arg Lys Gln Leu Val Pro Leu Leu Tyr Lys Gln Phe
        35                  40                  45

Val Pro Ser Met Pro Glu Arg Thr Leu Gly Ala Ser Gly Pro Ala Glu
    50                  55                  60

Gly Arg Val Thr Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly

```
                    290                 295                 300
Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
                340                 345                 350

Ala His Arg Ala Phe Ala Pro Leu Arg Leu Leu His Ala Leu Gly Ala
                355                 360                 365

Leu Leu Pro Gly Gly Ala Val Gln Pro Thr Gly Met His Trp Tyr Ser
370                 375                 380

Arg Leu Leu Tyr Arg Leu Ala Glu Glu Leu Met Gly
385                 390                 395

<210> SEQ ID NO 12
<211> LENGTH: 411
<212> TYPE: PRT
<213> ORGANISM: Mus musculus

<400> SEQUENCE: 12

Met Ser Pro Ala Trp Leu Arg Pro Arg Leu Arg Phe Cys Leu Phe Leu
1               5                   10                  15

Leu Leu Leu Leu Val Pro Ala Ala Arg Gly Cys Gly Pro Gly Arg
                20                  25                  30

Val Val Gly Ser Arg Arg Arg Pro Pro Arg Lys Leu Val Pro Leu Ala
                35                  40                  45

Tyr Lys Gln Phe Ser Pro Asn Val Pro Glu Lys Thr Leu Gly Ala Ser
                50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
                100                 105                 110

Ser Leu Ala Ile Ser Val Met Asn Gln Trp Pro Gly Val Lys Leu Arg
                115                 120                 125

Val Thr Glu Gly Arg Asp Glu Asp Gly His His Ser Glu Glu Ser Leu
                130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
                180                 185                 190

Glu His Ser Ala Ala Ala Lys Thr Gly Gly Cys Phe Pro Ala Gly Ala
                195                 200                 205

Gln Val Arg Leu Glu Asn Gly Glu Arg Val Ala Leu Ser Ala Val Lys
                210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
                260                 265                 270
```

-continued

```
Pro Ala His Leu Leu Phe Ile Ala Asp Asn His Thr Glu Pro Ala Ala
            275                 280                 285

His Phe Arg Ala Thr Phe Ala Ser His Val Gln Pro Gly Gln Tyr Val
        290                 295                 300

Leu Val Ser Gly Val Pro Gly Leu Gln Pro Ala Arg Val Ala Ala Val
305                 310                 315                 320

Ser Thr His Val Ala Leu Gly Ser Tyr Ala Pro Leu Thr Arg His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe Pro
        355                 360                 365

Ser Leu Ala Trp Gly Ser Trp Thr Pro Ser Glu Gly Val His Ser Tyr
370                 375                 380

Pro Gln Met Leu Tyr Arg Leu Gly Arg Leu Leu Glu Glu Ser Thr
385                 390                 395                 400

Phe His Pro Leu Gly Met Ser Gly Ala Gly Ser
                405                 410

<210> SEQ ID NO 13
<211> LENGTH: 437
<212> TYPE: PRT
<213> ORGANISM: Mus musculus

<400> SEQUENCE: 13

Met Leu Leu Leu Leu Ala Arg Cys Phe Leu Val Ile Leu Ala Ser Ser
  1               5                  10                  15

Leu Leu Val Cys Pro Gly Leu Ala Cys Gly Pro Gly Arg Gly Phe Gly
             20                  25                  30

Lys Arg Arg His Pro Lys Lys Leu Thr Pro Leu Ala Tyr Lys Gln Phe
         35                  40                  45

Ile Pro Asn Val Ala Glu Lys Thr Leu Gly Ala Ser Gly Arg Tyr Glu
     50                  55                  60

Gly Lys Ile Thr Arg Asn Ser Glu Arg Phe Lys Glu Leu Thr Pro Asn
 65                  70                  75                  80

Tyr Asn Pro Asp Ile Ile Phe Lys Asp Glu Glu Asn Thr Gly Ala Asp
                 85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Arg Leu Arg Val Thr Glu Gly
        115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240
```

```
Thr Phe Leu Asp Arg Asp Glu Gly Ala Lys Lys Val Phe Tyr Val Ile
            245                 250                 255

Glu Thr Leu Glu Pro Arg Glu Arg Leu Leu Thr Ala Ala His Leu
        260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
        290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
            325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
            355                 360                 365

Ala His Ala Leu Leu Ala Ala Leu Ala Pro Ala Arg Thr Asp Gly Gly
        370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
            405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 14
<211> LENGTH: 418
<212> TYPE: PRT
<213> ORGANISM: Brachydanio rerio

<400> SEQUENCE: 14

Met Arg Leu Leu Thr Arg Val Leu Leu Val Ser Leu Leu Thr Leu Ser
1               5                   10                  15

Leu Val Val Ser Gly Leu Ala Cys Gly Pro Gly Arg Gly Tyr Gly Arg
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
            100                 105                 110

Val Met Asn His Trp Pro Gly Val Lys Leu Arg Val Thr Glu Gly Trp
        115                 120                 125

Asp Glu Asp Gly His His Phe Glu Glu Ser Leu His Tyr Glu Gly Arg
    130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
```

```
            165                 170                 175
Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
            195                 200             205

Asp Gly Gly Gln Lys Ala Val Lys Asp Leu Asn Pro Gly Asp Lys Val
        210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
            275                 280                 285

Tyr Ala Ser Ser Val Arg Ala Gly Gln Lys Val Met Val Val Asp Asp
        290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Tyr Val Ser Ser
            355                 360                 365

Phe Leu Ser Pro Lys Thr Pro Ala Val Gly Pro Met Arg Leu Tyr Asn
370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser

<210> SEQ ID NO 15
<211> LENGTH: 475
<212> TYPE: PRT
<213> ORGANISM: Homo sapiens
<220> FEATURE:
<221> NAME/KEY: SITE
<222> LOCATION: (463)
<223> OTHER INFORMATION: Xaa=Gly, Ala, Val, Leu, Ile, Thr, or Ser

<400> SEQUENCE: 15

Met Leu Leu Leu Ala Arg Cys Leu Leu Leu Val Leu Val Ser Ser Leu
 1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95
```

```
Leu Met Thr Gln Arg Cys Lys Asp Lys Leu Asn Ala Leu Ala Ile Ser
            100                 105                 110
Val Met Asn Gln Trp Pro Gly Val Lys Leu Arg Val Thr Glu Gly Trp
            115                 120                 125
Asp Glu Asp Gly His His Ser Glu Glu Ser Leu His Tyr Glu Gly Arg
            130                 135                 140
Ala Val Asp Ile Thr Thr Ser Asp Arg Asp Arg Ser Lys Tyr Gly Met
145                 150                 155                 160
Leu Ala Arg Leu Ala Val Glu Ala Gly Phe Asp Trp Val Tyr Tyr Glu
                165                 170                 175
Ser Lys Ala His Ile His Cys Ser Val Lys Ala Glu Asn Ser Val Ala
            180                 185                 190
Ala Lys Ser Gly Gly Cys Phe Pro Gly Ser Ala Thr Val His Leu Glu
            195                 200                 205
Gln Gly Gly Thr Lys Leu Val Lys Asp Leu Ser Pro Gly Asp Arg Val
            210                 215                 220
Leu Ala Ala Asp Asp Gln Gly Arg Leu Leu Tyr Ser Asp Phe Leu Thr
225                 230                 235                 240
Phe Leu Asp Arg Asp Asp Gly Ala Lys Lys Val Phe Tyr Val Ile Glu
                245                 250                 255
Thr Arg Glu Pro Arg Glu Arg Leu Leu Leu Thr Ala Ala His Leu Leu
            260                 265                 270
Phe Val Ala Pro His Asn Asp Ser Ala Thr Gly Glu Pro Glu Ala Ser
            275                 280                 285
Ser Gly Ser Gly Pro Pro Ser Gly Gly Ala Leu Gly Pro Arg Ala Leu
            290                 295                 300
Phe Ala Ser Arg Val Arg Pro Gly Gln Arg Val Tyr Val Val Ala Glu
305                 310                 315                 320
Arg Asp Gly Asp Arg Arg Leu Leu Pro Ala Ala Val His Ser Val Thr
                325                 330                 335
Leu Ser Glu Glu Ala Ala Gly Ala Tyr Ala Pro Leu Thr Ala Gln Gly
            340                 345                 350
Thr Ile Leu Ile Asn Arg Val Leu Ala Ser Cys Tyr Ala Val Ile Glu
            355                 360                 365
Glu His Ser Trp Ala His Arg Ala Phe Ala Pro Phe Arg Leu Ala His
            370                 375                 380
Ala Leu Leu Ala Ala Leu Ala Pro Ala Arg Thr Asp Arg Gly Gly Asp
385                 390                 395                 400
Ser Gly Gly Gly Asp Arg Gly Gly Gly Arg Val Ala Leu Thr
                405                 410                 415
Ala Pro Gly Ala Ala Asp Ala Pro Gly Ala Gly Thr Ala Gly Ile
            420                 425                 430
His Trp Tyr Ser Gln Leu Leu Tyr Gln Ile Gly Thr Trp Leu Leu Asp
                435                 440                 445
Ser Glu Ala Leu His Pro Leu Gly Met Ala Val Lys Ser Ser Xaa Ser
            450                 455                 460
Arg Gly Ala Gly Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16
```

```
Met Ser Pro Ala Arg Leu Arg Pro Arg Leu His Phe Cys Leu Val Leu
 1               5                  10                  15

Leu Leu Leu Val Val Pro Ala Ala Trp Gly Cys Gly Pro Gly Arg
             20                  25                  30

Val Val Gly Ser Arg Arg Pro Arg Lys Leu Val Pro Leu Ala
         35                  40                  45

Tyr Lys Gln Phe Ser Pro Asn Val Pro Glu Lys Thr Leu Gly Ala Ser
     50                  55                  60

Gly Arg Tyr Glu Gly Lys Ile Ala Arg Ser Ser Glu Arg Phe Lys Glu
 65                  70                  75                  80

Leu Thr Pro Asn Tyr Asn Pro Asp Ile Ile Phe Lys Asp Glu Glu Asn
                 85                  90                  95

Thr Gly Ala Asp Arg Leu Met Thr Gln Arg Cys Lys Asp Arg Leu Asn
             100                 105                 110

Ser Leu Ala Ile Ser Val Met Asn Gln Trp Pro Gly Val Lys Leu Arg
             115                 120                 125

Val Thr Glu Gly Trp Asp Glu Asp Gly His His Ser Glu Glu Ser Leu
 130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                 165                 170                 175

Trp Val Tyr Tyr Glu Ser Lys Ala His Val His Cys Ser Val Lys Ser
                 180                 185                 190

Glu His Ser Ala Ala Lys Thr Gly Gly Cys Phe Pro Ala Gly Ala
                 195                 200                 205

Gln Val Arg Leu Glu Ser Gly Ala Arg Val Ala Leu Ser Ala Val Arg
     210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                 245                 250                 255

Phe Gln Val Ile Glu Thr Gln Asp Pro Pro Arg Arg Leu Ala Leu Thr
                 260                 265                 270

Pro Ala His Leu Leu Phe Thr Ala Asp Asn His Thr Glu Pro Ala Ala
             275                 280                 285

Arg Phe Arg Ala Thr Phe Ala Ser His Val Gln Pro Gly Gln Tyr Val
     290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                 325                 330                 335

Thr Leu Val Val Glu Asp Val Val Ala Ser Cys Phe Ala Ala Val Ala
             340                 345                 350

Asp His His Leu Ala Gln Leu Ala Phe Trp Pro Leu Arg Leu Phe His
             355                 360                 365

Ser Leu Ala Trp Gly Ser Trp Thr Pro Gly Glu Gly Val His Trp Tyr
370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                 405                 410
```

<210> SEQ ID NO 17
<211> LENGTH: 396
<212> TYPE: PRT
<213> ORGANISM: Homo sapiens

<400> SEQUENCE: 17

```
Met Ala Leu Leu Thr Asn Leu Leu Pro Leu Cys Cys Leu Ala Leu Leu
  1               5                  10                  15

Ala Leu Pro Ala Gln Ser Cys Gly Pro Gly Arg Gly Pro Val Gly Arg
             20                  25                  30

Arg Arg Tyr Ala Arg Lys Gln Leu Val Pro Leu Leu Tyr Lys Gln Phe
         35                  40                  45

Val Pro Gly Val Pro Glu Arg Thr Leu Gly Ala Ser Gly Pro Ala Glu
     50                  55                  60

Gly Arg Val Ala Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
    210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Trp Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380
```

```
Arg Leu Leu Tyr Arg Leu Ala Glu Glu Leu Leu Gly
385                 390                 395

<210> SEQ ID NO 18
<211> LENGTH: 416
<212> TYPE: PRT
<213> ORGANISM: Brachydanio rerio

<400> SEQUENCE: 18

Met Asp Val Arg Leu His Leu Lys Gln Phe Ala Leu Leu Cys Phe Ile
 1               5                  10                  15

Ser Leu Leu Thr Pro Cys Gly Leu Ala Cys Gly Pro Gly Arg Gly
                20                  25                  30

Tyr Gly Lys Arg Arg His Pro Lys Lys Leu Thr Pro Leu Ala Tyr Lys
                35                  40                  45

Gln Phe Ile Pro Asn Val Ala Glu Lys Thr Leu Gly Ala Ser Gly Lys
        50                  55                  60

Tyr Glu Gly Lys Ile Thr Arg Asn Ser Glu Arg Phe Lys Glu Leu Ile
 65                  70                  75                  80

Pro Asn Tyr Asn Pro Asp Ile Ile Phe Lys Asp Glu Glu Asn Thr Asn
                85                  90                  95

Ala Asp Arg Leu Met Thr Lys Arg Cys Lys Asp Lys Leu Asn Ser Leu
                100                 105                 110

Ala Ile Ser Val Met Asn His Trp Pro Gly Val Lys Leu Arg Val Thr
            115                 120                 125

Glu Gly Trp Asp Glu Asp Gly His His Leu Glu Glu Ser Leu His Tyr
        130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
                180                 185                 190

Ser Val Ala Ala Lys Ser Gly Gly Cys Phe Pro Gly Ser Gly Thr Val
            195                 200                 205

Thr Leu Gly Asp Gly Thr Arg Lys Pro Ile Lys Asp Leu Lys Val Gly
        210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
                260                 265                 270

His Leu Val Phe Val Gly Asn Ser Ala Ala Ser Gly Ile Thr Ala
            275                 280                 285

Thr Phe Ala Ser Asn Val Lys Pro Gly Asp Thr Val Leu Val Trp Glu
        290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
            340                 345                 350

Lys Trp Ala His Trp Ala Phe Ala Pro Val Arg Leu Cys His Lys Leu
```

```
                  355                 360                 365
Met Thr Trp Leu Phe Pro Ala Arg Glu Ser Asn Val Asn Phe Gln Glu
        370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415

<210> SEQ ID NO 19
<211> LENGTH: 1416
<212> TYPE: DNA
<213> ORGANISM: Drosophila melanogaster
<220> FEATURE:
<221> NAME/KEY: CDS
<222> LOCATION: (1)..(1413)

<400> SEQUENCE: 19 atg gat aac cac agc tca gtg cct tgg gcc agt gcc gcc agt gtc acc      48
Met Asp Asn His Ser Ser Val Pro Trp Ala Ser Ala Ala Ser Val Thr
1               5                   10                  15 tgt ctc tcc ctg gga tgc caa atg cca cag ttc cag ttc cag ttc cag      96
Cys Leu Ser Leu Gly Cys Gln Met Pro Gln Phe Gln Phe Gln Phe Gln
                20                  25                  30 ctc caa atc cgc agc gag ctc cat ctc cgc aag ccc gca aga aga acg     144
Leu Gln Ile Arg Ser Glu Leu His Leu Arg Lys Pro Ala Arg Arg Thr
            35                  40                  45 caa acg atg cgc cac att gcg cat acg cag cgt tgc ctc agc agg ctg     192
Gln Thr Met Arg His Ile Ala His Thr Gln Arg Cys Leu Ser Arg Leu
        50                  55                  60 acc tct ctg gtg gcc ctg ctg ctg atc gtc ttg ccg atg gtc ttt agc     240
Thr Ser Leu Val Ala Leu Leu Leu Ile Val Leu Pro Met Val Phe Ser
65                  70                  75                  80 ccg gct cac agc tgc ggt cct ggc cga gga ttg ggt cgt cat agg gcg     288
Pro Ala His Ser Cys Gly Pro Gly Arg Gly Leu Gly Arg His Arg Ala
                85                  90                  95 cgc aac ctg tat ccg ctg gtc ctc aag cag aca att ccc aat cta tcc     336
Arg Asn Leu Tyr Pro Leu Val Leu Lys Gln Thr Ile Pro Asn Leu Ser
            100                 105                 110 gag tac acg aac agc gcc tcc gga cct ctg gag ggt gtg atc cgt cgg     384
Glu Tyr Thr Asn Ser Ala Ser Gly Pro Leu Glu Gly Val Ile Arg Arg
        115                 120                 125 gat tcg ccc aaa ttc aag gac ctc gtg ccc aac tac aac agg gac atc     432
Asp Ser Pro Lys Phe Lys Asp Leu Val Pro Asn Tyr Asn Arg Asp Ile
130                 135                 140 ctt ttc cgt gac gag gaa ggc acc gga gcg gat ggc ttg atg agc aag     480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa     528
Arg Cys Lys Glu Lys Leu Asn Val Leu Ala Tyr Ser Val Met Asn Glu
                165                 170                 175 tgg ccc ggc atc cgg ctg ctg gtc acc gag agc tgg gac gag gac tac     576
Trp Pro Gly Ile Arg Leu Leu Val Thr Glu Ser Trp Asp Glu Asp Tyr
            180                 185                 190 cat cac ggc cag gag tcg ctc cac tac gag ggc cga gcg gtg acc att     624
His His Gly Gln Glu Ser Leu His Tyr Glu Gly Arg Ala Val Thr Ile
        195                 200                 205 gcc acc tcc gat cgc gac cag tcc aaa tac ggc atg ctc gct cgc ctg     672
Ala Thr Ser Asp Arg Asp Gln Ser Lys Tyr Gly Met Leu Ala Arg Leu
210                 215                 220 gcc gtc gag gct gga ttc gat tgg gtc tcc tac gtc agc agg cgc cac     720
```

-continued

| | | |
|---|---|---|
| Ala Val Glu Ala Gly Phe Asp Trp Val Ser Tyr Val Ser Arg Arg His<br>225                              230                       235                     240 | | |
| atc tac tgc tcc gtc aag tca gat tcg tcg atc agt tcc cac gtg cac<br>Ile Tyr Cys Ser Val Lys Ser Asp Ser Ser Ile Ser Ser His Val His<br>                      245                     250                    255 | 768 | |
| ggc tgc ttc acg ccg gag agc aca gcg ctg ctg gag agt gga gtc cgg<br>Gly Cys Phe Thr Pro Glu Ser Thr Ala Leu Leu Glu Ser Gly Val Arg<br>                  260                     265                    270 | 816 | |
| aag ccg ctc ggc gag ctc tct atc gga gat cgt gtt ttg agc atg acc<br>Lys Pro Leu Gly Glu Leu Ser Ile Gly Asp Arg Val Leu Ser Met Thr<br>        275                     280                    285 | 864 | |
| gcc aac gga cag gcc gtc tac agc gaa gtg atc ctc ttc atg gac cgc<br>Ala Asn Gly Gln Ala Val Tyr Ser Glu Val Ile Leu Phe Met Asp Arg<br>290                              295                     300 | 912 | |
| aac ctc gag cag atg caa aac ttt gtg cag ctg cac acg gac ggt gga<br>Asn Leu Glu Gln Met Gln Asn Phe Val Gln Leu His Thr Asp Gly Gly<br>305                              310                    315                    320 | 960 | |
| gca gtg ctc acg gtg acg ccg gct cac ctg gtt agc gtt tgg cag ccg<br>Ala Val Leu Thr Val Thr Pro Ala His Leu Val Ser Val Trp Gln Pro<br>                      325                     330                    335 | 1008 | |
| gag agc cag aag ctc acg ttt gtg ttt gcg cat cgc atc gag gag aag<br>Glu Ser Gln Lys Leu Thr Phe Val Phe Ala His Arg Ile Glu Glu Lys<br>                  340                     345                    350 | 1056 | |
| aac cag gtg ctc gta cgg gat gtg gag acg ggc gag ctg agg ccc cag<br>Asn Gln Val Leu Val Arg Asp Val Glu Thr Gly Glu Leu Arg Pro Gln<br>        355                     360                    365 | 1104 | |
| cga gtg gtc aag ttg ggc agt gtg cgc agt aag ggc gtg gtc gcg ccg<br>Arg Val Val Lys Leu Gly Ser Val Arg Ser Lys Gly Val Val Ala Pro<br>370                              375                     380 | 1152 | |
| ctg acc cgc gag ggc acc att gtg gtc aac tcg gtg gcc gcc agt tgc<br>Leu Thr Arg Glu Gly Thr Ile Val Val Asn Ser Val Ala Ala Ser Cys<br>385                              390                    395                  400 | 1200 | |
| tat gcg gtg atc aac agt cag tcg ctg gcc cac tgg gga ctg gct ccc<br>Tyr Ala Val Ile Asn Ser Gln Ser Leu Ala His Trp Gly Leu Ala Pro<br>                      405                     410                    415 | 1248 | |
| atg cgc ctg ctg tcc acg ctg gag gcg tgg ctg ccc gcc aag gag cag<br>Met Arg Leu Leu Ser Thr Leu Glu Ala Trp Leu Pro Ala Lys Glu Gln<br>                  420                     425                    430 | 1296 | |
| ttg cac agt tcg ccg aag gtg gtg agc tcg gcg cag cag cag aat ggc<br>Leu His Ser Ser Pro Lys Val Val Ser Ser Ala Gln Gln Gln Asn Gly<br>        435                     440                    445 | 1344 | |
| atc cat tgg tat gcc aat gcg ctc tac aag gtc aag gac tac gtg ctg<br>Ile His Trp Tyr Ala Asn Ala Leu Tyr Lys Val Lys Asp Tyr Val Leu<br>450                              455                    460 | 1392 | |
| ccg cag agc tgg cgc cac gat tga<br>Pro Gln Ser Trp Arg His Asp<br>465                              470 | 1416 | |

<210> SEQ ID NO 20
<211> LENGTH: 471
<212> TYPE: PRT
<213> ORGANISM: Drosophila melanogaster

<400> SEQUENCE: 20

Met Asp Asn His Ser Ser Val Pro Trp Ala Ser Ala Ser Val Thr
1                   5                   10                 15

Cys Leu Ser Leu Gly Cys Gln Met Pro Gln Phe Gln Phe Gln Phe Gln
                 20                  25                   30

Leu Gln Ile Arg Ser Glu Leu His Leu Arg Lys Pro Ala Arg Arg Thr
        35                     40                    45

-continued

```
Gln Thr Met Arg His Ile Ala His Thr Gln Arg Cys Leu Ser Arg Leu
    50                  55                  60

Thr Ser Leu Val Ala Leu Leu Ile Val Leu Pro Met Val Phe Ser
65                  70                  75                  80

Pro Ala His Ser Cys Gly Pro Gly Arg Gly Leu Gly Arg His Arg Ala
                85                  90                  95

Arg Asn Leu Tyr Pro Leu Val Leu Lys Gln Thr Ile Pro Asn Leu Ser
                100                 105                 110

Glu Tyr Thr Asn Ser Ala Ser Gly Pro Leu Glu Gly Val Ile Arg Arg
            115                 120                 125

Asp Ser Pro Lys Phe Lys Asp Leu Val Pro Asn Tyr Asn Arg Asp Ile
        130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
                180                 185                 190

His His Gly Gln Glu Ser Leu His Tyr Glu Gly Arg Ala Val Thr Ile
        195                 200                 205

Ala Thr Ser Asp Arg Asp Gln Ser Lys Tyr Gly Met Leu Ala Arg Leu
    210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
            260                 265                 270

Lys Pro Leu Gly Glu Leu Ser Ile Gly Asp Arg Val Leu Ser Met Thr
        275                 280                 285

Ala Asn Gly Gln Ala Val Tyr Ser Glu Val Ile Leu Phe Met Asp Arg
290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
            340                 345                 350

Asn Gln Val Leu Val Arg Asp Val Glu Thr Gly Glu Leu Arg Pro Gln
        355                 360                 365

Arg Val Val Lys Leu Gly Ser Val Arg Ser Lys Gly Val Val Ala Pro
    370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
            420                 425                 430

Leu His Ser Ser Pro Lys Val Val Ser Ser Ala Gln Gln Asn Gly
        435                 440                 445

Ile His Trp Tyr Ala Asn Ala Leu Tyr Lys Val Lys Asp Tyr Val Leu
    450                 455                 460
```

-continued

```
Pro Gln Ser Trp Arg His Asp
465                 470

<210> SEQ ID NO 21
<211> LENGTH: 221
<212> TYPE: PRT
<213> ORGANISM: Artificial Sequence
<220> FEATURE:
<223> OTHER INFORMATION: Description of Artificial Sequence: Degenerate
      Shh polypeptide general formula
<221> NAME/KEY: SITE
<222> LOCATION: (7)
<223> OTHER INFORMATION: Xaa=Gly, Ala, Val, Leu, Ile, Phe, Tyr, or Trp
<221> NAME/KEY: SITE
<222> LOCATION: (9)
<223> OTHER INFORMATION: Xaa=Arg, His or Lys
<221> NAME/KEY: SITE
<222> LOCATION: (44)
<223> OTHER INFORMATION: Xaa=Gly, Ala, Val, Leu, Ile, Ser. or Thr
<221> NAME/KEY: SITE
<222> LOCATION: (85)
<223> OTHER INFORMATION: Xaa=Gly, Ala, Val, Leu, Ile, Ser, or Thr
<221> NAME/KEY: SITE
<222> LOCATION: (93)
<223> OTHER INFORMATION: Xaa=Lys, Arg, His, Asn, or Gln
<221> NAME/KEY: SITE
<222> LOCATION: (98)
<223> OTHER INFORMATION: Xaa=Lys, Arg or His
<221> NAME/KEY: SITE
<222> LOCATION: (112)
<223> OTHER INFORMATION: Xaa=Ser, Thr, Tyr, Trp, or Phe
<221> NAME/KEY: SITE
<222> LOCATION: (132)
<223> OTHER INFORMATION: Xaa=Lys, Arg or His
<221> NAME/KEY: SITE
<222> LOCATION: (137)
<223> OTHER INFORMATION: Xaa=Met, Cys, Ser, or Thr
<221> NAME/KEY: SITE
<222> LOCATION: (139)
<223> OTHER INFORMATION: Xaa=Gly, Ala, Val, Leu, Ile, Ser, or Thr
<221> NAME/KEY: SITE
<222> LOCATION: (181)
<223> OTHER INFORMATION: Xaa=Leu, Val, Met, Thr, or Ser
<221> NAME/KEY: SITE
<222> LOCATION: (183)
<223> OTHER INFORMATION: Xaa=His, Phe, Tyr, Ser, Thr, Met, or Cys
<221> NAME/KEY: SITE
<222> LOCATION: (185)
<223> OTHER INFORMATION: Xaa=Gln, Asn, Glu, or Asp
<221> NAME/KEY: SITE
<222> LOCATION: (186)
<223> OTHER INFORMATION: Xaa=His, Phe, Tyr, Thr, Gln, Asn, Glu, or Asp
<221> NAME/KEY: SITE
<222> LOCATION: (189)
<223> OTHER INFORMATION: Xaa=Gln, Asn, Glu, Asp, Thr, Ser, Met, or Cys
<221> NAME/KEY: SITE
<222> LOCATION: (191)
<223> OTHER INFORMATION: Xaa=Ala, Gly, Cys, Leu, Val, or Met
<221> NAME/KEY: SITE
<222> LOCATION: (196)
<223> OTHER INFORMATION: Xaa=Arg, Lys, Met, Ile, Asn, Asp, Glu, Gln,
      Ser, Thr, or Cys
<221> NAME/KEY: SITE
<222> LOCATION: (200)
<223> OTHER INFORMATION: Xaa=Arg, Lys, Met, or Ile
<221> NAME/KEY: SITE
<222> LOCATION: (206)
<223> OTHER INFORMATION: Xaa=Ala, Gly, Cys, Asp, Glu, Gln, Asn, Ser,
      Thr, or Met
<221> NAME/KEY: SITE
<222> LOCATION: (207)
<223> OTHER INFORMATION: Xaa=Ala, Gly, Cys, Asp, Asn, Glu, or Gln
<221> NAME/KEY: SITE
<222> LOCATION: (209)
<223> OTHER INFORMATION: Xaa=Arg, Lys, Met, Ile, Asn, Asp, or Glu
<221> NAME/KEY: SITE
<222> LOCATION: (211)
<223> OTHER INFORMATION: Xaa=Leu, Val, Met, or Ile
```

-continued

```
<221> NAME/KEY: SITE
<222> LOCATION: (212)
<223> OTHER INFORMATION: Xaa=Phe, Tyr, Thr, His, or Trp
<221> NAME/KEY: SITE
<222> LOCATION: (216)
<223> OTHER INFORMATION: Xaa=Ile, Val, Leu, or Met
<221> NAME/KEY: SITE
<222> LOCATION: (217)
<223> OTHER INFORMATION: Xaa=Met, Cys, Ile, Leu, Val, Thr, or Ser
<221> NAME/KEY: SITE
<222> LOCATION: (219)
<223> OTHER INFORMATION: Xaa=Leu, Val, Met, Thr, or Ser

<400> SEQUENCE: 21

Cys Gly Pro Gly Arg Gly Xaa Gly Xaa Arg Arg His Pro Lys Lys Leu
  1               5                  10                  15

Thr Pro Leu Ala Tyr Lys Gln Phe Ile Pro Asn Val Ala Glu Lys Thr
             20                  25                  30

Leu Gly Ala Ser Gly Arg Tyr Glu Gly Lys Ile Xaa Arg Asn Ser Glu
         35                  40                  45

Arg Phe Lys Glu Leu Thr Pro Asn Tyr Asn Pro Asp Ile Ile Phe Lys
     50                  55                  60

Asp Glu Asn Thr Gly Ala Asp Arg Leu Met Thr Gln Arg Cys Lys
 65                  70                  75                  80

Asp Lys Leu Asn Xaa Leu Ala Ile Ser Val Met Asn Xaa Trp Pro Gly
                 85                  90                  95

Val Xaa Leu Arg Val Thr Glu Gly Trp Asp Glu Asp Gly His His Xaa
                100                 105                 110

Glu Glu Ser Leu His Tyr Glu Gly Arg Ala Val Asp Ile Thr Thr Ser
            115                 120                 125

Asp Arg Asp Xaa Ser Lys Tyr Gly Xaa Leu Xaa Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
            195                 200                 205

Xaa Leu Xaa Xaa Ser Asp Phe Xaa Xaa Phe Xaa Asp Arg
210                 215                 220

<210> SEQ ID NO 22
<211> LENGTH: 167
<212> TYPE: PRT
<213> ORGANISM: Artificial Sequence
<220> FEATURE:
<223> OTHER INFORMATION: Description of Artificial Sequence: Degenerate
      hedgehog polypeptide general formula
<221> NAME/KEY: SITE
<222> LOCATION: (7)
<223> OTHER INFORMATION: Xaa=Gly, Ala, Val, Leu, Ile, Pro, Phe, or Tyr
<221> NAME/KEY: SITE
<222> LOCATION: (8)
<223> OTHER INFORMATION: Xaa=Gly, Ala, Val, Leu, or Ile
<221> NAME/KEY: SITE
<222> LOCATION: (9)
<223> OTHER INFORMATION: Xaa=Gly, Ala, Val, Leu, Ile, Lys, His, or Arg
<221> NAME/KEY: SITE
<222> LOCATION: (12)
<223> OTHER INFORMATION: Xaa=Lys, Arg or His
<221> NAME/KEY: SITE
<222> LOCATION: (13)
```

```
<223> OTHER INFORMATION: Xaa=Phe, Trp or Tyr or an amino acid gap
<221> NAME/KEY: SITE
<222> LOCATION: (14)
<223> OTHER INFORMATION: Xaa=Gly, Ala, Val, Leu, or Ile or an amino acid
      gap
<221> NAME/KEY: SITE
<222> LOCATION: (17)
<223> OTHER INFORMATION: Xaa=Asn, Gln, His, Arg, or Lys
<221> NAME/KEY: SITE
<222> LOCATION: (19)
<223> OTHER INFORMATION: Xaa=Gly, Ala, Val, Leu, Ile, Ser, or Thr
<221> NAME/KEY: SITE
<222> LOCATION: (22)
<223> OTHER INFORMATION: Xaa=Gly, Ala, Val, Leu, Ile, Ser, or Thr
<221> NAME/KEY: SITE
<222> LOCATION: (27)
<223> OTHER INFORMATION: Xaa=Gly, Ala, Val, Leu, Ile, Ser, or Thr
<221> NAME/KEY: SITE
<222> LOCATION: (29)
<223> OTHER INFORMATION: Xaa=Ser, Thr, Gln, or Asn
<221> NAME/KEY: SITE
<222> LOCATION: (30)
<223> OTHER INFORMATION: Xaa=Met, Cys, Gly, Ala, Val, Leu, Ile, Ser, or
      Thr
<221> NAME/KEY: SITE
<222> LOCATION: (31)
<223> OTHER INFORMATION: Xaa=Gly, Alka, Val, Leu, Ile, or Pro
<221> NAME/KEY: SITE
<222> LOCATION: (33)
<223> OTHER INFORMATION: Xaa=Arg, His or Lys
<221> NAME/KEY: SITE
<222> LOCATION: (40)
<223> OTHER INFORMATION: Xaa=Gly, Ala, Val, Leu, Ile, Pro Arg, His, or
      Lys
<221> NAME/KEY: SITE
<222> LOCATION: (41)
<223> OTHER INFORMATION: Xaa=Gly, Ala, Val, Leu, Ile, Phe, or Tyr
<221> NAME/KEY: SITE
<222> LOCATION: (44)
<223> OTHER INFORMATION: Xaa=Arg, His or Lys
<221> NAME/KEY: SITE
<222> LOCATION: (45)
<223> OTHER INFORMATION: Xaa=Gly, Ala, Val, Leu, Ile, Ser, or Thr
<221> NAME/KEY: SITE
<222> LOCATION: (46)
<223> OTHER INFORMATION: Xaa=Thr or Ser
<221> NAME/KEY: SITE
<222> LOCATION: (48)
<223> OTHER INFORMATION: Xaa=Gly, Ala, Val, Leu, Ile, Asn, or Gln
<221> NAME/KEY: SITE
<222> LOCATION: (53)
<223> OTHER INFORMATION: Xaa=Arg, His or Lys
<221> NAME/KEY: SITE
<222> LOCATION: (54)
<223> OTHER INFORMATION: Xaa=Asp or Glu
<221> NAME/KEY: SITE
<222> LOCATION: (71)
<223> OTHER INFORMATION: Xaa=Ser or Thr
<221> NAME/KEY: SITE
<222> LOCATION: (79)
<223> OTHER INFORMATION: Xaa=Glu, Asp, Gln, or Asn
<221> NAME/KEY: SITE
<222> LOCATION: (83)
<223> OTHER INFORMATION: Xaa=Glu or Asp
<221> NAME/KEY: SITE
<222> LOCATION: (84)
<223> OTHER INFORMATION: Xaa=Arg, His or Lys
<221> NAME/KEY: SITE
<222> LOCATION: (85)
<223> OTHER INFORMATION: Xaa=Gly, Ala, Val, Leu, or Ile
<221> NAME/KEY: SITE
<222> LOCATION: (87)
<223> OTHER INFORMATION: Xaa=Gly, Ala, Val, Leu, Ile, Thr, or Ser
<221> NAME/KEY: SITE
<222> LOCATION: (95)
<223> OTHER INFORMATION: Xaa=Met, Cys, Gln, Asn, Arg, Lys, or His
<221> NAME/KEY: SITE
<222> LOCATION: (100)
<223> OTHER INFORMATION: Xaa=Arg, His or Lys
```

```
<221> NAME/KEY: SITE
<222> LOCATION: (107)
<223> OTHER INFORMATION: Xaa=Trp, Phe, Tyr, Arg, His, or Lys
<221> NAME/KEY: SITE
<222> LOCATION: (114)
<223> OTHER INFORMATION: Xaa=Gly, Ala, Val, Leu, Ile, Ser, Thr, Tyr, or
      Phe
<221> NAME/KEY: SITE
<222> LOCATION: (115)
<223> OTHER INFORMATION: Xaa=Gln, Asn, Asp, or Glu
<221> NAME/KEY: SITE
<222> LOCATION: (116)
<223> OTHER INFORMATION: Xaa=Asp or Glu
<221> NAME/KEY: SITE
<222> LOCATION: (125)
<223> OTHER INFORMATION: Xaa=Gly, Ala, Val, Leu, or Ile
<221> NAME/KEY: SITE
<222> LOCATION: (134)
<223> OTHER INFORMATION: Xaa=Arg, His or Lys
<221> NAME/KEY: SITE
<222> LOCATION: (135)
<223> OTHER INFORMATION: Xaa=Asn, Gln, Thr, or Ser
<221> NAME/KEY: SITE
<222> LOCATION: (139)
<223> OTHER INFORMATION: Xaa=Gly, Ala, Val, Leu, Ile, Ser, Thr, Met, or
      Cys
<221> NAME/KEY: SITE
<222> LOCATION: (141)
<223> OTHER INFORMATION: Xaa=Gly, Ala, Val, Leu, Ile, Thr, or Ser
<221> NAME/KEY: SITE
<222> LOCATION: (157)
<223> OTHER INFORMATION: Xaa=Arg, His or Lys
<221> NAME/KEY: SITE
<222> LOCATION: (158)
<223> OTHER INFORMATION: Xaa=Asn, Gln, Gly, Ala, Val, Leu, or Ile
<221> NAME/KEY: SITE
<222> LOCATION: (160)
<223> OTHER INFORMATION: Xaa=Gly, Ala, Val, Leu, or Ile
<221> NAME/KEY: SITE
<222> LOCATION: (162)..(162)
<223> OTHER INFORMATION: Xaa=Gly, Ala, Val, Leu, Ile, Ser, Thr, or Cys
<221> NAME/KEY: SITE
<222> LOCATION: (166)
<223> OTHER INFORMATION: Xaa=Gly, Ala, Val, Leu, Ile, Thr, or Ser
<221> NAME/KEY: SITE
<222> LOCATION: (167)
<223> OTHER INFORMATION: Xaa=Asp or Glu

<400> SEQUENCE: 22

Cys Gly Pro Gly Arg Gly Xaa Xaa Arg Arg Xaa Xaa Xaa Pro Lys
 1               5                  10                  15

Xaa Leu Xaa Pro Leu Xaa Tyr Lys Gln Phe Xaa Pro Xaa Xaa Xaa Glu
            20                  25                  30

Xaa Thr Leu Gly Ala Ser Gly Xaa Xaa Glu Gly Xaa Xaa Xaa Arg Xaa
        35                  40                  45

Ser Glu Arg Phe Xaa Xaa Leu Thr Pro Asn Tyr Asn Pro Asp Ile Ile
    50                  55                  60

Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
                85                  90                  95

Pro Gly Val Xaa Leu Arg Val Thr Glu Gly Xaa Asp Glu Asp Gly His
            100                 105                 110

His Xaa Xaa Xaa Ser Leu His Tyr Glu Gly Arg Ala Xaa Asp Ile Thr
        115                 120                 125

Thr Ser Asp Arg Asp Xaa Xaa Lys Tyr Gly Xaa Leu Xaa Arg Leu Ala
    130                 135                 140

Val Glu Ala Gly Phe Asp Trp Val Tyr Tyr Glu Ser Xaa Xaa His Xaa
145                 150                 155                 160
```

His Xaa Ser Val Lys Xaa Xaa
            165

<210> SEQ ID NO 23
<211> LENGTH: 74
<212> TYPE: DNA
<213> ORGANISM: Artificial Sequence
<220> FEATURE:
<223> OTHER INFORMATION: Description of Artificial Sequence: Primer

<400> SEQUENCE: 23
gcgcgcttcg aagcgaggca gccagcgagg gagagagcga gcgggcgagc cggagcgagg     60
aaatcgatgc gcgc                                                      74

<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: Primer

<400> SEQUENCE: 24
gcgcgcagat ctgggaaagc gcaagagaga gcgcacacgc acacaccccgc cgcgcgcact    60 cgggatccgc gcgc                                                      74

<210> SEQ ID NO 25
<211> LENGTH: 996
<212> TYPE: DNA
<213> ORGANISM: Artificial Sequence
<220> FEATURE:
<223> OTHER INFORMATION: Description of Artificial Sequence: Gene
      activation construct

<400> SEQUENCE: 25
cgaagcgagg cagccagcga gggagagagc gagcgggcga gccggagcga ggaaatcgaa     60
ggttcgaatc cttcccccac caccatcact ttcaaaagtc cgaaagaatc tgctccctgc    120
ttgtgtgttg gaggtcgctg agtagtgcgc gagtaaaatt taagctacaa caaggcaagg    180
cttgaccgac aattgcatga agaatctgct tagggttagg cgttttgcgc tgcttcgcga    240
tgtacgggcc agatatacgc gttgacattg attattgact agttattaat agtaatcaat    300
tacggggtca ttagttcata gcccatatat ggagttccgc gttacataac ttacggtaaa    360
tggcccgcct ggctgaccgc ccaacgaccc cgcccattg acgtcaataa tgacgtatgt     420
tcccatagta acgccaatag ggactttcca ttgacgtcaa tgggtggact atttacggta    480
aactgcccac ttggcagtac atcaagtgta tcatatgcca gtacgccccc tattgacgt    540 caatgacggt aaatggcccg cctggcatta tgcccagtac atgaccttat gggactttcc   600
tacttggcag tacatctacg tattagtcat cgctattacc atggtgatgc ggttttggca    660
gtacatcaat gggcgtggat agcggtttga ctcacgggga tttccaagtc tccacccat     720 tgacgtcaat gggagtttgt tttggcacca aaatcaacgg gactttccaa aatgtcgtaa    780
caactccgcc ccattgacgc aaatgggcgg taggcgtgta cggtgggagg tctatataag    840
cagagctctc tggctaacta gagaacccac tgcttactgg cttatcgaaa ttaatacgac    900
tcactatagg gagacccaag cttggtaccg agctcggatc gatctgggaa agcgcaagag    960
agagcgcaca cgcacacacc cgccgcgcgc actcgg                              996

<210> SEQ ID NO 26

-continued

```
<211> LENGTH: 26
<212> TYPE: DNA
<213> ORGANISM: Artificial Sequence
<220> FEATURE:
<223> OTHER INFORMATION: Description of Artificial Sequence: Antisense
      construct

<400> SEQUENCE: 26
gtcctggcgc cgccgccgcc gtcgcc                                           26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Antisense
      construct

<400> SEQUENCE: 27
ttccgatgac cggcctttcg cggtga                                           26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Antisense
      construct

<400> SEQUENCE: 28
gtgcacggaa aggtgcaggc cacact                                           26
```

METHODS AND COMPOSITIONS FOR REGULATING LYMPHOCYTE ACTIVITY

PRIORITY INFORMATION

This application claims priority to U.S. Provisional Application 60/168,112, filed Nov. 30, 1999.

BACKGROUND OF THE INVENTION

The lymphoid system performs critical functions in animals that include preventing and combating infection, and surveillance and immune elimination of tumor cells. Loss of immune function leads to an immunocompromised status that can predispose the host to serious and life-threatening disease. Functional abnormalities may be present in any of the elements that participate in mediating an immune response, e.g., cellular or humoral elements such as granulocytes, lymphocytes, complement, antibody, or cytokines.

The immune system is a network of cells adapted to protect the organism against pathogens and cells that are not recognized as "self." Once the immune system is activated, it enlists the participation of a variety of cells and molecules to mount an effector function designed to eliminate the "non-self" entity within the body. Lymphocytes are cells of the immune system that are capable of specifically recognizing and selectively eliminating foreign entities. By contrast to other cells of the immune system, such as neutrophils which are considered non-specific in their reactions to invaders, the characteristics of lymphocytes confer specificity, diversity, memory and self/nonself recognition to the immune response.

There are two major populations of lymphocytes: B lymphocytes and T lymphocytes. B lymphocytes originate and mature within the bone marrow and are responsible for formation of antibody molecules. T lymphocytes also arise from the bone marrow but mature in the thymus. There are two major subpopulations of T-cells: T helper cells and T cytotoxic cells. The two types of T cells can be distinguished by the presence of one of two membrane glycoproteins, either CD4 or CD8. The T-helper cells (which express CD4) when activated by antigen-complexes (foreign molecules coupled to special proteins) respond by secreting various growth factors known collectively as cytokines. These cytokines are signals that activate other cells of the immune system, including the T-cytotoxic cells. The T-cytotoxic cells (which express CD8) when activated, proliferate and differentiate into cytotoxic T lymphocytes (CTL) which are able to monitor for and eliminate from the body pathogenic cells, foreign cells, virus-infected cells, and tumor cells.

The normal development, maturation and differentiation of T lymphocytes are regulated by various peptide factors.

SUMMARY OF THE INVENTION

The present invention provides methods and compositions for modulating the immune function of an animal by administering an agent which mimics, or alternatively inhibits, hedgehog-mediated signal transduction. Thus, the subject method can be used as an immunosuppressive, e.g., by administering a hedgehog agonist, or as an immunostimulatant, e.g., by administering a hedgehog antagonist.

Wherein the subject method is carried out using a hedgehog therapeutic, the hedgehog therapeutic preferably a polypeptide including a hedgehog portion comprising at least a bioactive extracellular portion of a hedgehog protein, e.g., the hedgehog portion includes at least 50, 100 or 150 (contiguous) amino acid residues of an N-terminal half of a hedgehog protein. In preferred embodiments, the hedgehog portion includes at least a portion of the hedgehog protein corresponding to a 19 kd fragment of the extracellular domain of a hedgehog protein.

In preferred embodiments, the hedgehog portion has an amino acid sequence at least 60, 75, 85, or 95 percent identical with a hedgehog protein of any of SEQ ID Nos. 10–18 or 20, though sequences identical to those sequence listing entries are also contemplated as useful in the present method. The hedgehog portion can be encoded by a nucleic acid which hybridizes under stringent conditions to a nucleic acid sequence of any of SEQ D Nos. 1–9 or 19, e.g., the hedgehog portion can be encoded by a vertebrate hedgehog gene, especially a human hedgehog gene.

In other embodiments, the subject method can be carried out by administering a gene activation construct, wherein the gene activation construct is deigned to recombine with a genomic hedgehog gene of the patient to provide a heterologous transcriptional regulatory sequence operatively linked to a coding sequence of the hedgehog gene.

In still other embodiments, the subject method can be practiced with the administration of a gene therapy construct encoding a hedgehog polypeptide. For instance, the gene therapy construct can be provided in a composition selected from a group consisting of a recombinant viral particle, a liposome, and a poly-cationic nucleic acid binding agent.

In yet other embodiments, the subject method can be carried out using a ptc therapeutic. An exemplary ptc therapeutic is a small organic molecule which binds to a patched protein and derepresses patched-mediated inhibition of mitosis, e.g., a molecule which binds to patched and mimics hedgehog-mediated patched signal transduction, which binds to patched and regulates patched-dependent gene expression. For instance, the binding of the ptc therapeutic to patched may result in upregulation of patched and/or gli expression.

In a more generic sense, the ptc therapeutic can be a small organic molecule which interacts with MK cells to induce hedgehog-mediated patched signal transduction, such as by altering the localization, protein—protein binding and/or enzymatic activity of an intracellular protein involved in a patched signal pathway. For instance, the ptc therapeutic may alter the level of expression of a hedgehog protein, a patched protein or a protein involved in the intracellular signal transduction pathway of patched.

In certain embodiments, the ptc therapeutic is an antisense construct which inhibits the expression of a protein which is involved in the signal transduction pathway of patched and the expression of which antagonizes hedgehog-mediated signals. The antisense construct is perferably an oligonucleotide of about 20–30 nucleotides in length and having a GC content of at least 50 percent.

In other embodiments, the ptc therapeutic is an inhibitor of protein kinase A (PKA), such as a 5-isoquinolinesulfonamide. The PKA inhibitor can be a cyclic AMP analog. Exemplary PKA inhibitors include N-[2-((p-bromocinnamyl)amino)ethyl]-5-isoquinolinesulfonamide, 1-(5-isoquinoline-sulfonyl)-2-methylpiperazine, KT5720, 8-bromo-cAMP, dibutyryl-cAMP and PKA Heat Stable Inhibitor isoform α. Another exemplary PKA inhibitor is represented in the general formula:

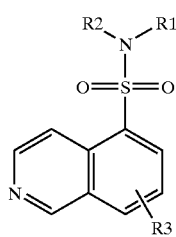

wherein,

R₁ and R₂ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-O$-lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$, or R₁ and R₂ taken together with N form a heterocycle (substituted or unsubstituted);

R₃ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $-(CH_2)_m-R_8$, $-(CH_2)_m-OH$, $-(CH_2)_m-O$-lower alkyl, $-(CH_2)_m-O$-lower alkenyl, $-(CH_2)_n-O-(CH_2)_m-R_8$, $-(CH_2)_m-SH$, $-(CH_2)_m-S$-lower alkyl, $-(CH_2)_m-S$-lower alkenyl, $-(CH_2)_n-S-(CH_2)_m-R_8$;

R₈ represents a substituted or unsubstituted aryl, aralkyl, cycloalkyl, cycloalkenyl, or heterocycle; and n and m are independently for each occurrence zero or an integer in the range of 1 to 6.

DETAILED DESCRIPTION OF THE INVENTION

I. Overview

Figure 1:
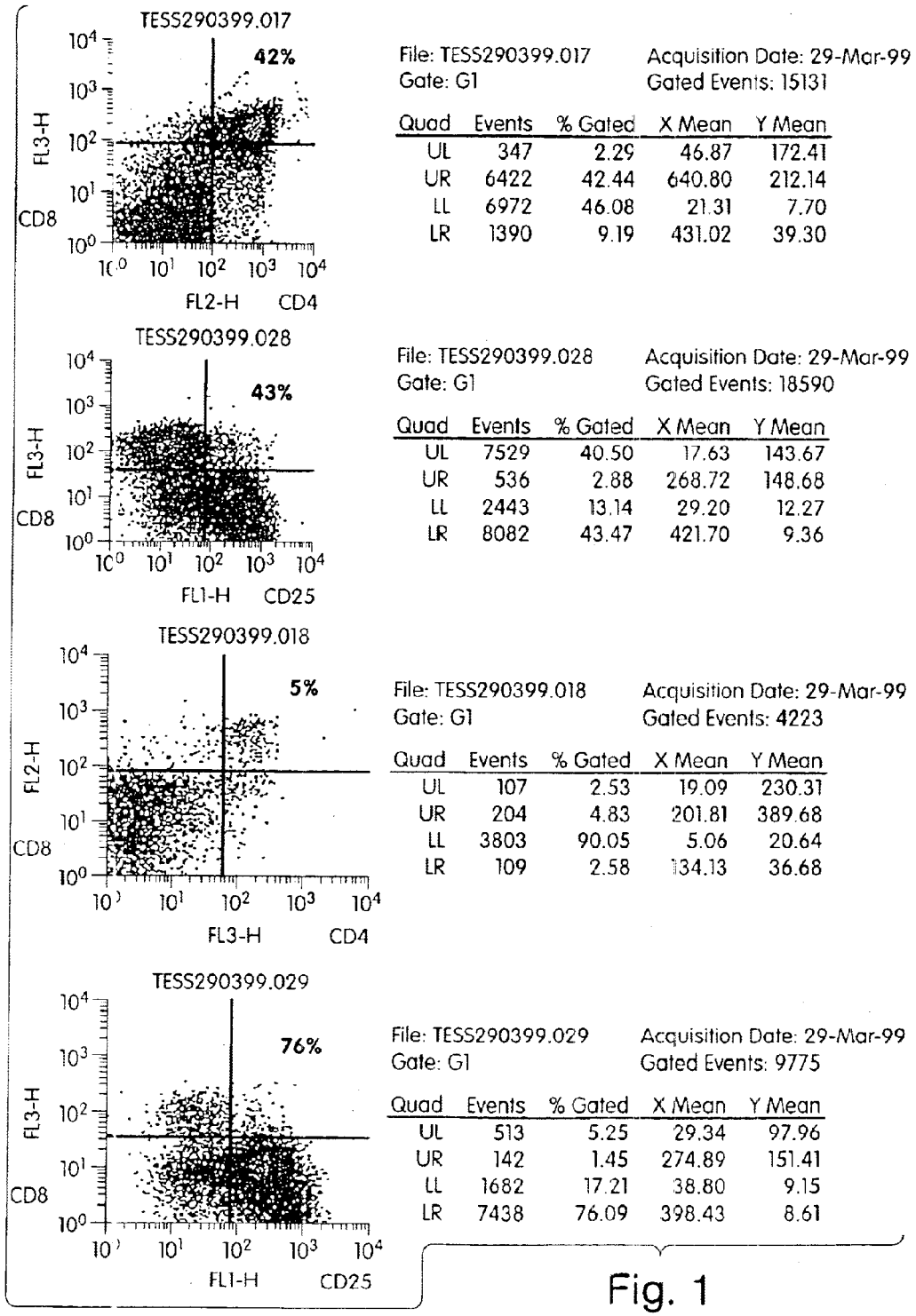
FIGS. 1–4 illustrate the profile for staining with various markers for T-cell maturity.

The present application is directed to the discovery that hedgehog gene products are able to regulate maturation of T lymphocytes. Certain aspects of the invention are directed to preparations of hedgehog polypeptides, or other molecules which regulate patched or smoothened signalling, and their uses as immunomodulatory agents against both acquired and hereditary immunological disorders.

For instance, such compositions can be used to increase the population of T-helper cells to optimum levels in the host, e.g, to stimulate the immune system of the animal. Such uses of the subject compoistions can be used in the treatment of bacterial or viral infections, as well as to help the body fight against cancer cells. Alternatively, these substances also enable the host to adjust to diseases arising from disarrangement of self-recognition processes in which there is excessive attack by host T-cells against endogenous tissues. In such instances, the subject compositions can be used to reduce T-cell population so that the signs and symptoms of self-directed inflammatory (autoimmune) diseases such rheumatoid arthritis and multiple sclerosis are ameliorated.

As described herein, hedgehog proteins inhibit maturation of T lymphocytes. Based upon its inhibitory effect, the administration of hedgehog or ptc therapeutics (defined infra) is suggested herein as a treatment for several types of immunological disorders involving unwanted activation of cellular immunity, e.g., graft rejection, autoimmune disorders, and the like. In other embodiments, inhibitors of hedgehog signalling pathways can be used as immunostimulatory agents, e.g., to counteract the effects of any endogenous activation of a hedgehog/ptc pathway.

In general, the method of the present invention comprises administering to animal, or to cultured lymphocytes in vitro, an amount of a hedgehog or ptc therapeutic which produces a non-toxic response by the cell of inhibition of maturation (in the case of a hedgehog agonist) or promotion of T cell maturation (in the case of a hedgehog antagonist). The subject method can be carried out on cells which may be either dispersed in culture or a part of an intact tissue or organ. Moreover, the method can be performed on cells which are provided in culture (in vitro), or on cells in a whole animal (in vivo).

In one aspect, the present invention provides pharmaceutical preparations and methods for treating or preventing hyperimmune or hypoimmune disorders utilizing, as an active ingredient, a hedgehog polypeptide or a mimetic thereof. The invention also relates to methods of controlling the functional performance of T cells by use of the pharmaceutical preparations of the invention.

The subject hedgehog treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

Without wishing to be bound by any particular theory, the inhibitory effect of hedgehog on T cell maturation may be due at least in part to the ability of hedgehog proteins to antagonize (directly or indirectly) patched-mediated regulation of gene expression and other physiological effects mediated by that protein. The patched gene product, a cell surface protein, is understood to signal through a pathway which causes transcriptional repression of members of the Wnt and Dpp/BMP families of morphogens, proteins which impart positional information. In other tissue, the introduction of hedgehog relieves (derepresses) this inhibition conferred by patched, allowing expression of particular gene programs.

Recently, it has been reported that mutations in the human version of patched, a gene first identified in a fruit fly developmental pathway, cause a hereditary skin cancer and may contribute to sporadic skin cancers. See, for example, Hahn et al. (1996) *Cell* 86: 841–851; and Johnson et al., (1996) *Science* 272: 1668–1671. The demonstraction that nevoid basal-cell carcinoma (NBCC) results from mutations in the human patched gene provided an example of the roles patched plays in post-embryonic deveolpment. These observations have led the art to understand one activity of patched to be a tumor suppressor gene, which may act by inhibiting proliferative signals from hedgehog. Our observations set forth below reveal potential new roles for the hedgehog/patched pathway in maintenance of mature T-cells and other lyphocytic cell lines. Accordingly, the present invention contemplates the use of other agents which are capable of mimicking or antagonizing, depending on the desired consequence, the effect of the hedgehog protein on patched signalling, e.g., as may be identified from the drug screening assays described below.

II. Definitions

For convience, certain terms employed in the specfication, examples, and appended claims are collected here.

The term "hedgehog therapeutic" refers to various forms of hedgehog polypeptides, as well as peptidomimetics, which can modulate the proliferation/differentiation state of lymphocytes, by, as will be clear from the context of individual examples, mimicing or potentiating (agonizing) or inhibiting (antagonizing) the effects of a naturally-occurring hedgehog protein. A hedgehog therapeutic which mimics or potentiates the activity of a wild-type hedgehog protein is a "hedgehog agonist". Conversely, a hedgehog therapeutic which inhibits the activity of a wild-type hedgehog protein is a "hedgehog antagonist". In particular, the term "hedgehog polypeptide" encompasses preparations of hedgehog proteins and peptidyl fragments thereof, both agonist and antagonist forms as the specific context will make clear.

As used herein the term "bioactive fragment of a hedgehog protein" refers to a fragment of a full-length hedgehog polypeptide, wherein the fragment specifically agonizes or antagonizes inductive events mediated by wild-type hedgehog proteins. The hedgehog biactive fragment preferably is a soluble extracellular portion of a hedgehog protein, where solubility is with reference to physiologically compatible solutions. Exemplary bioactive fragments are described in PCT publications WO 95/18856 and WO 96/17924.

The term "ptc therapeutic" refers to agents which either (i) mimic the effect of hedgehog proteins on patched signalling, e.g., which antagonize the cell-cycle inhibitory and/or T-cell maturation promoting activity of patched, or (ii) activate or potentiate patched signalling. In other embodiments, the ptc therapeutic can be a hedgehog antagonist. The ptc therapeutic can be, e.g., a peptide, a nucleic acid, a carbohydrate, a small organic molecule, or natural product extract (or fraction thereof).

An "effective amount" of, e.g., a hedgehog or ptc therapeutic, with respect to the subject method of treatment, refers to an amount of a composition, e.g., a hedgehog polypeptide, in a preparation which, when applied as part of a desired dosage regimen brings enhances or inhibits (as the case may be) T-cell maturation, relative to the absence of the hedgehog or ptc therapeutic, according to clinically acceptable standards for the disorder to be treated.

A "patient" or "subject" to be treated by the subject method can mean either a human or non-human animal.

The "growth state" of a cell refers to the rate of proliferation of the cell and the state of differentiation of the cell.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be refered to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with an hedgeog sequence of the present invention.

The term "corresponds to", when referring to a particular polypeptide or nucleic acid sequence is meant to indicate that the sequence of interest is identical or homologous to the reference sequence to which it is said to correspond.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in tun used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$-$(hh)_m$—$(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

The term "CD4$^+$ lymphocyte" is intended to mean a lymphocyte having a plurality of cell surface CD4 molecules as evidenced by binding of an antibody specific for CD4 to the cell surface, e.g., monoclonal antibody OKT4 (Ortho Diagnostics, Piscataway, N.J.).

The term "CD8+ lymphocyte" is intended to mean a lymphocyte having a plurality of cell surface CD8 molecules as evidenced by binding of an antibody specific for CD8 to the cell surface, e.g., monoclonal antibody OKT8 (Ortho Diagnostics, Piscataway, N.J.).

"Peripheral blood leukocytes", abbreviated PBL, are intended to mean the cellular components of the immune system in blood, e.g., lymphocytes, monocytes, eosinophils, basophils, neutrophils, plasma cells, mast cell precursors, and the like.

"Lymphocytes" are intended to encompass T-lymphocytes, (also referred to as T-cells), B-lymphocytes (also referred to as B-cells), natural killer-lymphocytes (NK-cells), cytotoxic T lymphocytes (CTL), T-helper lymphocytes, delta gamma-T-cell receptor bearing cells as well as precursors and activated derivatives thereof.

"Activated lymphocyte" is intended to mean that subset of lymphocytes which has been i) exposed to a stimulus, and ii) has been triggered to change from a metabolically-quiescent cell into a cell with increased protein synthesis and/or DNA and RNA synthesis and possibly cell division. Illustrative stimuli and triggering pathways leading to activated lymphocytes include interaction of T cell receptors with antigens, interaction of interleukin receptors with interleukins, interaction of growth factor receptors with growth factors, interaction of lymphocyte cell surface determinants with antibody (e.g., anti-CD2) or mitogens (e.g., PHA), and the like.

"Subject in need thereof" is intended to mean a mammal having one or more clinical or laboratory indicia of a disorder or disease. The subject may exhibit clinical disease activity or may have a subclinical or latent infection. Subjects in need thereof include human and non-human primates, mammals, domestic animals, livestock, and the like, e.g., dogs, cats, rodents, birds, horses, cows, pigs and fish.

III. Exemplary Applications of Method and Compositions

According to the invention, preparations with ptc and hedgehog therapeutics are used in immunoregulatory disorders and diseases in animals and humans, for the prevention or prophylaxis, control, diagnosis or treatment thereof.

The subject method has wide applicability to the treatment or prophylaxis of disorders affecting the regulation of lymphocytes, particularly maturation and/or activation of T lymphocytes. In general, the method can be characterized as including a step of administering to an animal an amount of a ptc or hedgehog therapeutic effective to alter the proliferative and/or differentiation state of treated lymphocytes. Such therapeutic compositions may be useful in treatments designed to modulate, e.g., increase or decrease, an immunological response. Such diseases and conditions include, but are not limited to, infection (such as bacterial or viral infection), metabolic disease such as diabetes, nutritional deficiency, toxic agents, graft rejection or other hyperacute response, or autoimmune disorders. The goals of treatment in each case can be twofold: (1) to eliminate the cause of the disease or unwanted immunological response, and (2) to relieve its symptoms.

In view of their immunosuppressant activity, the hedgehog proteins (and agonists thereof) are suitable for preventing and treating diseases and conditions which require a temporary or permanent reduction or suppression of an immune response. In particular, their use extends to suppressing the activation of the proliferation of lymphocytes or cytotoxic T-cells and/or immunocytes, e.g. for preventing or treating autoimmune diseases such as diseases of the rheumatic type, multiple sclerosis, psoriasis, atopic dermatitis, or for preventing the rejection of transplanted tissues or organs such as kidneys, heart, lungs, bone marrow, spleen, skin or cornea, in undesirable reactions during or after transfusions, allergic diseases, particularly those which affect the gastrointestinal tract and which may take the form of an inflammation, or inflammatory, proliferative and hyperproliferative diseases and cutaneous manifestations of immunological disorders such as eczematous dermatitis, urticaria, vasculitis and scleroderma.

Thus, it is particularly advantageous to use immunosuppressive forms of the subject hedgehog nd ptc therapeutics clinically for the disorders, diseases and conditions described above, i.e. when it is desirable to achieve immunosuppression in an animal or human body.

Depending on the nature and cause of the disease or disorder to be treated or the condition which is to be influenced in an animal or human body, it may be desirable to administer the hedgehog or ptc therapeutic preparation systemically, locally or topically to the tissue or organ in question. Systemic action is desirable, for example, when various organs or organ systems are in need of treatment, as is the case for example in systemic autoimmune diseases or allergies or in transplants of large, foreign organs or tissues. By contrast, a local effect would be considered if only local manifestations of an immunological occurrence had to be treated, e.g. in small transplants of skin or cornea or in cases of local dermatitis.

Depending on the duration and intensity of the immunosuppressant activity required, the hedgehog or ptc therapeutic preparations may be given one or more times a day, as well as intermittently, over a period of several days, weeks or months and in various dosages.

In still other embodiments, antagonist (lymphocyte maturation promoting) forms of the subject ptc and hedgehog therapeutics can be used to treat disorders involving hypoimmunity, e.g., immunosuppressed or immunocompromised patients. For instance, the effect of hedgehog-induced immunosuppression, e.g., resulting from endogenous or heterologous activation of the hedgehog signalling pathway, can be counteracted using antagonist forms of the subject ptc and hedgehog therapeutics.

Thus, the subject method contemplates the treatment of immunocompromised subjects to increase one or more indicia of cell mediated immunity (CMI), humoral immunity, or innate resistance to infection, by administering pharmaceutical preparations of an activating ptc or hedgehog therapeutic. In certain embodiments, such immunity-promoting activities of antagonists forms of the subject ptc and hedgehog therapeutics can be identified, e.g., by i) increased E-rosette forming cells (E-RFC) in thymocyte cultures after incubation with the subject ptc or hedgehog therapeutic agents; ii) increased E-RFC in cultures of thymocytes from aged animals after incubation with the subject ptc or hedgehog therapeutic agents; and, iii) increased expression of OKT 4<+> in cultures of human peripheral blood T-lymphocytes from patients with secondary immunodeficiency syndromes following treatment with the subject ptc or hedgehog therapeutic agents. Increased expression of CD2 and CD4 accessory molecules on T-lymphocytes is compatible with a heighten the state of innate or induced immunity to infection, e.g., by upregulating T-helper and cytotoxic T-lymphocytes to respond to lower levels of antigen.

Immunodeficiency states fall into three general etiologic categories. First, there is immunosuppression that occurs as a consequence of disease processes. Second, there are immunodeficiencies that arise because of therapy for other diseases, so-called iatrogenic immunodeficiencies. Third, immunodeficiencies may result from direct attack of T-lymphocytes by the human immunodeficiency virus (HIV) that causes the acquired immunodeficiency syndrome (AIDS).

Common disease processes that lead to immunodeficiency are malnutrition, neoplasias, aging, and infections. Malnourished people, patients with advanced widespread cancers and people with debilitating illnesses become sick and die more often because impaired cell-mediated and humoral immune responses increase susceptibility to infections by a variety of organisms. A state of generalized deficiency in immune responses is called anergy. Various types of infections, especially viral infections, lead to immunosuppression. A drug such as a maturation-pormoting form of a Ptc or hedgehog therapeutic, e.g., capable of making the T-helper lymphocyte components of the immune system more robust, will be an important therapeutic agent for increasing the resistance of the patient to infections. For example, Ptc or hedgehog therapeutic or its analogs, may be:

administered to patients, especially older patients, before or just after admissions to hospitals in order to reduce the risks of nosocomial (hospital-induced) infections, a common and severe clinical problem administered to burn victims, because such individuals are especially prone to infections administered to patients in anticipation of epidemic infections, for example, in conjunction with influenza vaccinations or hepatitis vaccinations, to invigorate the immune response to pathogens administered to patients with asymptomatic viral infections, in order to enhance immune surveillance of pathogenic organisms and reduce the likelihood of recurrence of disease, for example, for individuals who are carriers of herpes viruses, varicella viruses, hepatitis viruses and HIV.

Iatrogenic immunosuppression is most often due to drug therapies which either kill or functionally inactivate lymphocytes. Various chemotherapeutic drugs are administered to cancer patients, and these drugs are usually cytotoxic to both mature and developing lymphocytes as well as to granulocyte and monocyte precursors. Thus, cancer chemotherapy is almost always accompanied by a period of immunosuppression and increased risk of infections. Radiation treatment of cancer carries the same risks. Medications (granulocyte-colony stimulating factor) exist for increasing neutrophils in blood to combat infections that occur after cancer chemotherapy, but no medications are currently used for restoring lymphocytic functions. Major surgery, for example repair of aneurysms or by-pass operations, also decrease immune function in humans. The reasons for the decline in blood lymphocytes that occur because of major surgery are not clear, but an agent that elevates lymphocyte functions in such patients have therapeutic value in decreasing the likelihood of infections.

One final form of acquired immunosuppression that should be mentioned results from the absence of a spleen, caused by surgical removal of the organ after trauma or for the treatment of certain hematologic diseases or as a result of infarction in sickle cell disease. Patients without spleens are more susceptible to infections by some organisms, particularly encapsulated bacteria such as *Streptococcus pneumoniae*. The spleen is apparently required for the induction of protective humoral immune responses to such organisms. The subject Ptc or hedgehog therapeutics can help individuals without a spleen or without a thymus in resistance against infection by micro-organisms.

IV. Exemplary Hedgehog Therapeutic Compounds.

The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The various naturally-occurring hedgehog proteins from which the subject therapeutics can be derived are characterized by a signal peptide, a highly conserved N-terminal region, and a more divergent C-terminal domain. In addition to signal sequence cleavage in the secretory pathway (Lee, J. J. et al. (1992) *Cell* 71: 33–50; Tabata, T. et al. (1992) *Genes Dev.* 2635–2645; Chang, D. E. et al. (1994) *Development* 120: 3339–3353), hedgehog precursor proteins naturally undergo an internal autoproteolytic cleavage which depends on conserved sequences in the C-terminal portion (Lee et al. (1994) *Science* 266: 1528–1537; Porter et al. (1995) *Nature* 374: 363–366). This autocleavage leads to a 19 kD N-terminal peptide and a C-terminal peptide of 26–28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15: 2294–2303; Porter et al. (1995) supra; Ekker, S. C. et al. (1995) *Curr. Biol.* 5: 944–955; Lai, C. J. et al. (1995) *Development* 121: 2349–2360). The N-terminal peptide stays tightly associated with the surface of cells in which it was synthesized, while the C-terminal peptide is freely diffusible both in vitro and in vivo (Lee et al. (1994) supra; Bumcrot el al. (1995) supra; Mart', E. et al. (1995) *Development* 121: 2537–2547; Roelink, H. et al. (1995) *Cell* 81: 445–455). Cell surface retention of the N-terminal peptide is dependent on autocleavage, as a truncated form of hedgehog encoded by an RNA which terminates precisely at the normal position of internal cleavage is diffusible in vitro (Porter et al. (1995) supra) and in vivo (Porter, J. A. et al. (1996) *Cell* 86, 21–34). Biochemical studies have shown that the autoproteolytic cleavage of the hedgehog precursor protein proceeds through an internal thioester intermediate which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

The vertebrate family of hedgehog genes includes at least four members, e.g., paralogs of the single *drosophila* hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No: 1; a mouse Dhh polypeptide is encoded by SEQ ID No: 2; a mouse Ihh polypeptide is encoded by SEQ ID No: 3; a mouse Shh polypeptide is encoded by SEQ ID No: 4 a zebrafish Shh polypeptide is encoded by SEQ ID No: 5; a human Shh polypeptide is encoded by SEQ ID No: 6; a human Ihh polypeptide is encoded by SEQ ID No: 7; a human Dhh polypeptide is encoded by SEQ ID No. 8; and a zebrafish Thh is encoded by SEQ ID No. 9.

TABLE 1

Guide to hedgehog sequences in Sequence Listing

| | Nucleotide | Amino Acid |
|---|---|---|
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| Zebrafish Thh | SEQ ID No. 9 | SEQ ID No. 18 |
| Drosophila HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein.

In addition to proteolytic fragmentation, the vertebrate hedgehog proteins can also be modified post-translationally, such as by glycosylation and/or addition of lipophilic moieties, such as stents, fatty acids, etc., though bacterially produced (e.g. unmodified) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

There are a wide range of lipophilic moieties with which hedgehog polypeptides can be derivatized. The term "lipophilic group", in the context of being attached to a hedgehog polypeptide, refers to a group having high hydrocarbon content thereby giving the group high affinity to lipid phases. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, sterols, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

In one embodiment, the hedgehog polypeptide is modified with one or more sterol moieties, such as cholesterol. See, for example, PCT publication WO 96/17924. In certain embodiments, the cholesterol is preferably added to the C-terminal glycine were the hedgehog polypeptide corresponds to the naturally-occurring N-terminal proteolytic fragment.

In another embodiment, the hedgehog polypeptide can be modified with a fatty acid moiety, such as a myrostoyl, palmitoyl, stearoyl, or arachidoyl moiety. See, e.g., Pepinsky et al. (1998) *J. Biol. Chem* 273: 14037.

In addition to those effects seen by cholesterol-addition to the C-terminus or fatty acid addition to the N-terminus of extracellular fragments of the protein, at least certain of the biological activities of the hedgehog gene products are unexpectedly potentiated by derivativation of the protein with lipophilic moieties at other sites on the protein and/or by moieties other than cholesterol or fatty acids. Certain aspects of the invention are directed to the use of preparations of hedgehog polypeptides which are modified at sites other than N-terminal or C-terminal residues of the natural processed form of the protein, and/or which are modified at such terminal residues with lipophilic moieties other than a sterol at the C-terminus or fatty acid at the N-terminus.

Particularly useful as lipophilic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1–C18)-alkyl phosphate diesters, —O—CH$_2$—CH(OH)—O—(C12–C18)-alkyl, and in particular conjugates with pyrene derivatives. The lipophilic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3' tetramethylindocarbocyanine perchlorate, octadecyl rhodamine B and the BODIPY dyes available from Molecular Probes Inc.

Other exemplary lipophilic moietites include aliphatic carbonyl radical groups include 1-or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbornaneacetyl, bicyclo[2.2.2.]-oct-5-eneacetyl, 1-methoxybicyclo[2.2.2.]-oct-5-ene-2-carbonyl, cis-5-norbornene-endo-2,3-dicarbonyl, 5-norbornen-2-ylacetyl, (1R)-(−)-myrtentaneacetyl, 2-norbornaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

The hedgehog polypeptide can be linked to the hydrophobic moiety in a number of ways including by chemical coupling means, or by genetic engineering.

There are a large number of chemical cross-linking agents that are known to those skilled in the art. For the present invention, the preferred cross-linking agents are heterobifunctional cross-linkers, which can be used to link the hedgehog polypeptide and hydrophobic moiety in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include: succinimidyl 4-(N-maleimidomethyl) cyclohexane-1-carboxylate (SMCC), m-Maleimidobenzoyl-N— hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl- a-methyl-a-(2-pyridyldithio) tolune (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate-2 HCl (DMP) are examples of useful homobifunctional cross-linking agents, and bis-[β-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a recent review of protein coupling techniques, see Means et al. (1990) *Bioconjugate Chemistry* 1: 2–12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's.

Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein—protein conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

The reaction buffer should be free of extraneous amines and sulfhydryls. The pH of the reaction buffer should be 7.0–7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the lipophilic group chosen for reaction with maleimides, activated halogens, or pyridyl disulfides must contain a free sulfhydryl. Alternatively, a primary amine may be modified with to add a sulfhydryl.

In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5–7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing lipophilic group under the appropriate buffer conditions. The conjugates can be isolated from the reaction mixture by methods such as gel filtration or by dialysis.

Exemplary activated lipophilic moieties for conjugation include: N-(-pyrene)maleimide; 2,5-dimethoxystilbene-4'-maleimide, eosin-5-maleimide; fluorescein-5-maleimide; N-(4-(6-dimethylamino-2-benzofuranyl)phenyl)maleimide; benzophenone-4-maleimide; 4-dimethylaminophenylazophenyl-4'-maleimide (DABMI), tetramethylrhodamine-5-maleimide, tetramethylrhodamine-6-maleimide, Rhodamine RedTM $C_2$ maleimide, N-(5-aminopentyl)maleimide, trifluoroacetic acid salt, N-(2-aminoethyl)maleimide, trifluoroacetic acid salt, Oregon GreenTM 488 maleimide, N-(2-((2-(((4-azido-2,3,5,6-tetrafluoro)benzoyl) amino)ethyl)dithio)ethyl)maleimide (TFPAM-SS1), 2-(1-(3-dimethylaminopropyl)-indol-3-yl)-3-(indol-3-yl) maleimide (bisindolylmaleimide; GF 109203x), BODIPY® FL N-(2-aminoethyl)maleimide, N-(7-dimethylamino-4-methylcoumarin-3-yl)maleimide (DACM), AlexaTM 488 $C_5$ maleimide, AlexaTM 594 $C_5$ maleimide, sodium saltN-(1-pyrene)maleimide, 2,5-dimethoxystilbene-4'-maleimide, eosin-5-maleimide, fluorescein-5-maleimide, N-(4-(6-dimethylamino-2-benzofuranyl)phenyl)maleimide, benzophenone-4-maleimide, 4-dimethylaminophenylazophenyl-4'-maleimide, 1-(2-maleimidylethyl)-4-(5-(4-methoxyphenyl) oxazol-2-yl)pyridinium methanesulfonate, tetramethylrhodamine-5-maleimide, tetramethylrhodamine-6-maleimide, Rhodamine RedTM C2 maleimide, N-(5-aminopentyl)maleimide, N-(2-aminoethyl)maleimide, N-(2-((2-(((4-azido-2,3,5,6-tetrafluoro)benzoyl) amino)ethyl) dithio)ethyl)maleimide, 2-(1-(3-dimethylaminopropyl)-indol-3-yl)-3-(indol-3-yl) maleimide, N-(7-dimethylamino-4-methylcoumarin-3-yl)maleimide (DACM), 11H-Benzo[a]fluorene, Benzo[a]pyrene.

In one embodiment, the hedgehog polypeptide can be derivatived using pyrene maleimide, which can be purchased from Molecular Probes (Eugene, Oreg.), e.g., N-(1-pyrene)maleimide or 1-pyrenemethyl iodoacetate (PMIA ester).

For those embodiments wherein the hydophobic moiety is a polypeptide, the modified hedgehog polypeptide of this invention can be constructed as a fusion protein, containing the hedgehog polypeptide and the hydrophobic moiety as one contiguous polypeptide chain.

In certain embodiments, the lipophilic moiety is an amphipathic polypeptide, such as magainin, cecropin, attacin, melittin, gramicidin S, alpha-toxin of *Staph. aureus*, alamethicin or a synthetic amphipathic polypeptide. Fusogenic coat proteins from viral particles can also be a convenient source of amphipathic sequences for the subject hedgehog proteins.

Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

In one embodiment, the hedgehog therapeutic is a polypeptide encodable by a nucleotide sequence that hybridizes under stringent conditions to a hedgehog coding sequence represented in one or more of SEQ D Nos:1–7. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from mRNA or genomic DNA samples using techniques Well known in the art. For example, a cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Preferred nucleic acids encode a hedgehog polypeptide comprising an amino acid sequence at least 60% homologous or identical, more preferably 70% homologous or identical, and most preferably 80% homologous or identical with an amino acid sequence selected from the group consisting of SEQ ID Nos:8–14. Nucleic acids which encode polypeptides at least about 90%, more preferably at least about 95%, and most preferably at least about 98–99% homology or identity with an amino acid sequence represented in one of SEQ ID Nos:8–14 are also within the scope of the invention.

In addition to native hedgehog proteins, hedgehog polypeptides preferred by the present invention are at least 60% homologous or identical, more preferably 70% homologous or identical and most preferably 80% homologous or identical with an amino acid sequence represented by any of SEQ ID Nos:8–14. Polypeptides which are at least 90%, more preferably at least 95%, and most preferably at least about 98–99% homologous or identical with a sequence selected from the group consisting of SEQ ID Nos:8–14 are also within the scope of the invention. The only prerequisite is that the hedgehog polypeptide is capable of modulating the growth state of T lymphocytes.

The term "recombinant protein" refers to a polypeptide of the present invention which is produced by recombinant DNA techniques, wherein generally, DNA encoding a hedgehog polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein" those proteins having an amino acid sequence of a native hedgehog protein, or an amino acid sequence similar thereto which is generated by mutations including substitutions and deletions (including truncation) of a naturally occurring form of the protein.

The method of the present invention can also be carried out using variant forms of the naturally occurring hedgehog polypeptides, e.g., mutational variants.

As is known in the art, hedgehog polypeptides can be produced by standard biological techniques or by chemical synthesis. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due to the presence of the pBR322 ori, and in *S. cerevisiae* due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ ID Nos: 1–7.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2-gpt, pSV2-neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,*

2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an hedgehog protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169: 751–757) and *Salmonella typhimurium* and its in vitro activity has been demonstrated on recombinant proteins (Miller et al. (1987) *PNAS* 84: 2718–1722). Therefore, removal of an N-terminal methionine, if desired, can be achieved either in vivo by expressing hedgehog-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-5-transferase (GST-fusion) proteins. Such GST-fusion proteins can enable easy purification of the hedgehog polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g. of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309: 30–3; and Komblihtt et al. (1985) *EMBO* 4: 1755–9) can be added to the hedgehog polypeptide to support attachment of the chimeric molecule to a cell through binding ECM components (Ruoslahti et al. (1987) *Science* 238: 491–497; Pierschbacher et al. (1987) *J. Biol. Chem.* 262: 17294–8; Hynes (1987) *Cell* 48: 549–54; and Hynes (1992) *Cell* 69: 11–25).

In a preferred embodiment, the hedgehog polypeptide is isolated from, or is otherwise substantially free of, other cellular proteins, especially other extracellular or cell surface associated proteins which may normally be associated with the hedgehog polypeptide, unless provided in the form of fusion protein with the hedgehog polypeptide. The term "substantially free of other cellular or extracellular proteins" (also referred to herein as "contaminating proteins") or "substantially pure preparations" or "purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID Nos: 10–18 or 20, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioctive fragments of hedgehog polypeptide, preferred hedgehog therapeutics includeat least 50 (contiguous) amino acid residues of a hedgehog polypeptide, more preferably at least 100 (contiguous), and even more preferably at least 150 (contiguous) residues.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24–197 of SEQ ID No. 15, 28–202 of SEQ ID No. 16, and 23–198 of SEQ ID No. 17. By "corresponding approximately" it is meant that the sequence of interest is at most 20 amino acid residues different in length to the reference sequence, though more preferably at most 5, 10 or 15 amino acid different in length.

As described above for recombinant polypeptides, isolated hedgehog polypeptides can include all or a portion of the amino acid sequences represented in SEQ ID No:8, SEQ ID No:9, SEQ ID No:10, SEQ ID No:11, SEQ ID No:12, SEQ ID No:13 or SEQ ID No:14, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

Still other preferred hedgehog polypeptides includes an amino acid sequence represented by the formula A-B wherein: (i) A represents all or the portion of the amino acid sequence designated by residues 1–168 of SEQ ID No:21; and B represents at least one amino acid residue of the amino acid sequence designated by residues 169–221 of SEQ ID No:21; (ii) A represents all or the portion of the amino acid sequence designated by residues 24–193 of SEQ ID No:15; and B represents at least one amino acid residue of the amino acid sequence designated by residues 194–250 of SEQ ID No:15; (iii) A represents all or the portion of the amino acid sequence designated by residues 25–193 of SEQ ID No:13; and B represents at least one amino acid residue of the amino acid sequence designated by residues 194–250 of SEQ ID No:13; (iv) A represents all or the portion of the amino acid sequence designated by residues 23–193 of SEQ ID No: 11; and B represents at least one amino acid residue of the amino acid sequence designated by residues 194–250 of SEQ ID No: 11; (v) A represents all or the portion of the amino acid sequence designated by residues 28–197 of SEQ ID No:12; and B represents at least one amino acid residue of the amino acid sequence designated by residues 198–250 of SEQ ID No:12; (vi) A represents all or the portion of the amino acid sequence designated by residues 29–197 of SEQ ID No:16; and B represents at least one amino acid residue of the amino acid sequence designated by residues 198–250 of SEQ ID No: 16; or (vii) A represents all or the portion of the amino acid sequence designated by residues 23–193 of SEQ ID No. 17, and B represents at least one amino acid residue of the amino acid sequence designated by residues 194–250 of SEQ ID No. 17. In certain preferred embodiments, A and B together represent a contiguous polypeptide sequence designated sequence, A represents at least 25, 50, 75, 100, 125 or 150 (contiguous) amino acids of the designated sequence, and B represents at least 5, 10, or 20 (contiguous) amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above. In preferred embodiments, the hedgehog polypeptide includes a C-terminal glycine (or other appropriate residue) which is derivatized with a cholesterol.

Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") hedgehog protein. For example, Roman et al. (1994) *Eur J Biochem* 222: 65–73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack N-glycosylation sites (e.g. to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that one could reasonably expect that certain isolated replacements of amino acids, e.g., replacement of an amino acid residue with another related amino acid (i.e. isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methionine. (see, for example, *Biochemistry*, 2nd ed., Ed. by L. Stryer, W H Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried using homologs of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g. homologs) that are functional in binding to a receptor for hedgehog proteins. The purpose of screening such combinatorial libraries is to generate, for example, novel hedgehog homologs which can act as either agonists or antagonist. To illustrate, hedgehog homologs can be engineered by the present method to provide more efficient binding to a cognate receptor, such as patched, yet still retain at least a portion of an activity associated with hedgehog. Thus, combinatorially-derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hedgehog by the present method can provide domains more suitable for use in fusion proteins, such as one that incorporates portions of other proteins which are derived from the extracellular matrix and/or which bind extracellular matrix components.

To further illustrate the state of the art of combinatorial mutagenesis, it is noted that the review article of Gallop et al. (1994) *J Med Chem* 37:1233 describes the general state of the art of combinatorial libraries as of the earlier 1990's. In particular, Gallop et al state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins: Structure, Function and Genetics* 8: 309–314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity. Indeed, it is the ability of combinatorial techniques to screen billions of different variants by high throughout analysis that removes any requirement of a priori understanding or knowledge of critical residues.

To illsutrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences in a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

C-G-P-G-R-G-X(1)-G-X(2)-R-R-H-P-K-K-L-T-P-L-A-Y-K-Q-F-I-P-N-V-A-E-K-T-L-G-A-S-G-R-Y-E-G-K-I-X(3)-R-N-S-E-R-F-K-E-L-T-P-N-Y-N-P-D-I-I-F-K-D-E-E-N-T-G-A-D-R-L-M-T-Q-R-C-K-D-K-L-N-X(4)-L-A-I-S-V-M-N-X(5)-W-P-G-V-X(6)-L-R-V-T-E-G-W-D-E-D-G-H-H-X(7)-E-E-S-L-H-Y-E-G-R-A-V-D-I-T-T-S-D-R-D-X(8)-S-K-Y-G-X(9)-L-X(10)-R-L-A-V-E-A-G-F-D-W-V-Y-Y-E-S-K-A-H-I-H-C-S-V-K-A-E-N-S-V-A-A-K-S-G-G-C-F-P-G-S-A-X(11)-V-X(12)-L-X(13)-X(14)-G-G-X(15)-K-X-(16)-V-K-D-L-X(17)-P-G-D-X(18)-V-L-A-A-D-X(19)-X(20)-G-X(21)-LX(22)-X(23)-S-D-F-X(24)-X(25)-F-X(26)-D-R (SEQ ID No: 21 wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp; Xaa(2) represents Arg, His or Lys; Xaa(3) represents Gly, Ala, Val, Leu, Ile, Ser or Thr, Xaa(4) represents Gly, Ala, Val, Leu, Ile, Ser or Thr; Xaa(5) represents Lys, Arg, His, Asn or Gin; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(l 1) represents Leu, Val, Met, Thr or Ser; Xaa(12) represents His, Phe, Tyr, Ser, Thr, Met or Cys; Xaa(13) represents Gln, Asn, Glu, or Asp; Xaa(14) represents His, Phe, Tyr, Thr, Gin, Asn, Glu or Asp; Xaa(15) represents Gln, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gin, Ser, Thr or Cys; Xaa(18) represents Arg, Lys, Met or Ile; Xaa(19) represents Ala, Gly, Cys, Asp, Glu, Gin, Asn, Ser, Thr or Met; Xaa(20) represents Ala, Gly, Cys, Asp, Asn, Glu or Gln; Xaa(21) represents Arg, Lys, Met, Ile, Asn, Asp, Glu or Gln; Xaa(22) represent Leu, Val, Met or Ile; Xaa(23) represents Phe, Tyr, Thr, His or Trp; Xaa(24) represents Ile, Val, Leu or Met; .Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

C-G-P-G-R-G-X(1)-X(2)-X(3)-R-R-X(4-X(5)-X(6)-P-K-X(7)-L-X(8)-P-L-X(9)-Y-K-Q-F-X(10)-P-X(11)-X(12)-X(13)-E-X(14)-T-L-G-A-S-G-X(15)-X(16)-E-G-X(17)-X(18)-X(9)-R-X(20)-S-E-R-F-X(21)-X(22-L-T-P-N-Y-N-P-D-I-I-F-K-D-E-E-N-X(23)-G-A-D-R-L-M-T-X(24)-R-C-K-X(25)-X(26)-X(27)-N-X(28)-L-A-I-S-V-M-N-X(29)-W-P-G-V-X(30)-L-R-V-T-E-G-X(31)-D-E-D-G-H-H-X(32)-X(33)-X(34)-S-L-H-Y-E-G-R-A-X(35)-D-I-T-T-S-D-R-D-X(36)-X(37-K-Y-G-X(38)-L-X(39)-R-L-A-V-E-A-G-F-D-W-V-Y-Y-E-S-X(40)-X(41)-H-X(42)-H-X(43)-S-V-K-X(44)-X(45) (SEQ ID No:22 wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gin, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr; Xaa(11) represents Ser, Thr, Gln or Asn; Xaa(12) represents Met, Cys, Gly, Ala, Val, Leu, Ile, Ser or Thr, Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gin; Xaa(21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser, Xaa(29) represents Met, Cys, Gin, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gin, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gin, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gin, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, SA (1983) *Tetrahedron* 39:3; Itakura et al. (1981) *Recombinant DNA, Proc* 3*rd Cleveland Sympos. Macromolecules*, ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249: 386–390; Roberts et al. (1992) *PNAS* 89: 2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g. the polypeptides of the library all include a signal sequence but no transmembrane or cytoplasmic domains), and is used to transfect a eukaryotic cell that can be co-cultured with peripehral nerve cells. A functional hedgehog protein secreted by the cells expressing the combinatorial library will diffuse to neighboring T lymphocytes and induce a particular biological response, such as proliferation or differentiation. The pattern of detection of such a change in phenotype will resemble a gradient function, and will allow the isolation (generally after several repetitive rounds of selection) of cells producing hedgehog homologs active as neurotrophic agents. Likewise, hedgehog antagonists can be selected in similar fashion by the ability of the cell producing a functional antagonist to protect neighboring cells (e.g., to inhibit proliferation) from the effect of wild-type hedgehog added to the culture media.

To illustrate, target T lymphocytes are cultured in 24-well microtitre plates. Other eukaryotic cells are transfected with the combinatorial hedgehog gene library and cultured in cell culture inserts (e.g. Collaborative Biomedical Products, Catalog #40446) that are able to fit into the wells of the microtitre plate. The cell culture inserts are placed in the wells such that recombinant hedgehog homologs secreted by the cells in the insert can diffuse through the porous bottom of the insert and contact the target cells in the microtitre plate wells. After a period of time sufficient for functional forms of a hedgehog protein to produce a measurable response in the target cells, such as growth state, the inserts are removed and the effect of the variant hedgehog proteins on the target cells determined. Cells from the inserts corresponding to wells which score positive for activity can be split and re-cultured on several inserts, the process being repeated until the active clones are identified.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) *Bio/Technology* 9: 1370–1371; and Goward et al. (1992) *TIBS* 18: 136–140). In a similar fashion, fluorescently labeled molecules which bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et. al., PCT publication WO 92/09690; Marks et al. (1992) *J. Biol. Chem.* 267: 16007–16010; Griffths et al. (1993) *EMBO J.* 12: 725–734; Clackson et al. (1991) *Nature* 352:624–628; and Barbas et al. (1992) *PNAS* 89:4457–4461).

In an illustrative embodiment, the recombinant phage antibody system (RPAS, Pharamacia Catalog number 27-9400-01) can be easily modified for use in expressing and =screening hedgehog combinatorial libraries. For instance, the pCANTAB 5 phagemid of the RPAS kit contains the gene which encodes the phage gIII coat protein. The hedgehog combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins which are capable of binding an hedgehog receptor are selected or enriched by panning. For instance, the phage library can be applied to cells which express the patched protein and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for hedgehog homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89: 7811–7815; Yourvan et al., 1992, *Parallel Problem Solving from Nature*, 2. In Maenner and Manderick, eds., Elsevir Publishing Co., Amsterdam, pp. 401–410; Delgrave et al., 1993, *Protein Engineering* 6 (3): 327–331).

The invention also provides for reduction of the hedgehog protein to generate mimetics, e.g. peptide or non-peptide agents, which are able to disrupt binding of a hedgehog polypeptide of the present invention with an hedgehog receptor. Thus, such mutagenic techniques as described above are also useful to map the determinants of the hedgehog proteins which participate in protein—protein interactions involved in, for example, binding of the subject hedgehog polypeptide to other extracellular matrix components. To illustrate, the critical residues of a subject hedgehog polypeptide which are involved in molecular recognition of an hedgehog receptor such as patched can be determined and used to generate hedgehog-derived peptidomimetics which competitively inhibit binding of the authentic hedgehog protein with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. Such mimetics may then be used to interfere with the normal function of a hedgehog protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, IL, 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Recombinantly produced forms of the hedgehog proteins can be produced using, e.g, expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either an agonistic or antagonistic form of a hedgehog polypeptide. Thus, another aspect of the invention features expression vectors for in vivo transfection of a hedgehog polypeptide in particular cell types so as cause ectopic expression of a hedgehog polypeptide in an T lymphocytes or other cells associated therewith.

Formulations of such expression constructs may be administered in any biologically effective carrier, e.g. any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types; including T lymphocytes, in vitro and/or in vivo (see for example Eglitis, et al. (1985) Science 230: 1395–1398; Danos and Mulligan (1988) Proc. Natl. Acad. Sci. USA 85: 6460–6464; Wilson et al. (1988) Proc. Natl. Acad. Sci. USA 85: 3014–3018; Armentano et al. (1990) Proc. Natl. Acad. Sci. USA 87: 6141–6145; Huber et al. (1991) Proc. Natl. Acad. Sci. USA 88: 8039–8043; Ferry et al. (1991) Proc. Natl. Acad. Sci. USA 88: 8377–8381; Chowdhury et al. (1991) Science 254: 1802–1805; van Beusechem et al. (1992) Proc. Natl. Acad. Sci. USA 89: 7640–7644; Kay et al. (1992) Human Gene Therapy 3: 641–647; Dai et al. (1992) Proc. Natl. Acad. Sci. USA 89: 10892–10895; Hwu et al. (1993) J. Immunol. 150: 4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) PNAS 86: 9079–9083; Julan et al. (1992) J Gen Virol 73: 3251–3255; and Goud et al (1983) Virology 163: 251–254); or coupling cell surface receptor ligands to the viral env proteins (Neda et al. (1991) J Biol Chem 266: 14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431434; and Rosenfeld et al. (1992) *Cell* 68: 143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including T lymphocytes. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A hedgehog expression construct can be delivered in a gene therapy construct to dermal cells by, e.g., electroporation using techniques described, for example, by Dev et al. ((1994) *Cancer Treat Rev* 20: 105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the hedgehog or ptc therapeutic can be a "gene activation" construct which, by homologous recombination with a genomic DNA, alters the transcriptional regulatory sequences of an endogenous gene. For instance, the gene activation construct can replace the endogenous promoter of a hedgehog gene with a heterologous promoter, e.g., one which causes consitutive expression of the hedgehog gene or which causes inducible expression of the gene under conditions different from the normal expression pattern of the gene. Other genes in the patched signaling pathway can be similarly targeted. A vareity of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous hedgehog gene (exon sequence, intron sequence, promoter sequences, etc.) which direct recombination and (2) heterologous transcriptional regulatory sequencers) which is to be operably linked to the coding sequence for the genomic hedgehog gene upon recombination of the gene activation construct. For use in generating cultures of hedgehog producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native hedgehog gene. Such insertion occurs by homologous recombination, i.e., recombination regions of the activation construct that are homologous to the endogenous hedgehog gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as consitutive or inducible promoters), enhancers, negative regualtory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, *J. Exp. Med.,* 169:13), the human β-actin promoter (Gunning et al. (1987) *PNAS* 84: 4831–4835), the glucocorticoid-inducible promoter present in the mouse mammary tumor virus long terminal repeat (MMTV LTR)(Klessig et al. (1984) *Mol. Cell Biol.* 4:13541362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bernoist et al. (1981) *Nature* 290:304310; Templeton et al. (1984) *Mol. Cell Biol.,* 4:817; and Sprague et al. (1983) *J. Virol.,* 45:773), the promoter contained in the 3' long terminal repeat of Rous sarcoma virus (RSV) (Yamamoto et al., 1980, *Cell,* 22: 787–797), the herpes simplex virus (HSV) thymidine kinase promoter/enhancer (Wagner et al. (1981) *PNAS* 82: 3567–71), and the herpes simplex virus LAT promoter (Wolfe et al. (1992) *Nature Genetics,* 1: 379–384).

In an exemplary embodiment, portions of the 5' flanking region of the human Shh gene are amplified using primers which add restriction sites, to generate the following fragments 5'-gcgcgcttcgaaGCGAGGCAGCCAGCGAGGG AGAGAGCGAGCGGGCGAGCCGAGC-GAGGAAatcgatgcgcgc (primer 1) (SEQ ID No. 23) 5'-gcgcgcagatctGGGAAAGCGCAAGAGAGAGCGCACA CGCACACACCCGCCGCGCG-CACTCGggatccgcgcgc (primer 2) (SEQ ID No. 24).

As illustrated, primer 1 includes a 5' non-coding region of the human Shh gene and is flanked by an AsuII and ClaI restriction sites. Primer 2 includes a portion of the 5' non-coding region immediately 3' to that present in primer 1. The hedgehog gene sequence is flanked by XhoII and BamHI restriction sites. The purified amplimers are cut with each of the enzymes as appropriate.

The vector pCDNA1.1 (Invitrogen) includes a CMV promoter. The plasmid is cut with with AsuII, which cleaves just 3' to the CMV promoter sequence. The AsuII/ClaI fragment of primer 1 is ligated to the AsuII cleavage site of the pcDNA vector. The ClaI/AsuII ligation destroys the AsuII site at the 3' end of a properly inserted primer 1.

The vector is then cut with BamHI, and an XhoII/BamHI fragment of primer 2 is ligated to the BamHI cleavage site. As above, the BamHI/XhoII ligation destroys the BamHI site at the 5' end of a properly inserted primer 2.

Individual colonies are selected, cut with AsuII and BamHI, and the size of the AsuII/BamHI fragment determined. Colonies in which both the primer 1 and primer 2 sequences are correctly inserted are further amplified, an cut with AsuII and BamHI to produce the gene activation construct cgaagcgaggcagccagcgagg-gagagagcgagcgggcgagccggagc-gaggaaATCGAAGGTTCGAATCCTTC CCCCACCAC-CATCACTTTCAAAAGTCCGAAAGAATCTGCTCCCTG CTTGTGTGTTGG AGGTCGCTGAGTAGTGCGCGAG-TAAAATTTAAGCTACAACAAGGCAAGGCTTGACC GACAATTGCATGAAGAATCTGCT-TAGGGTTAGGCGTTTGCGCTGCTCGCGATGTA CGGGCCAGATATACGCGTTGACATTGAT-TATTGACTAGTTATFAATAGTAATCAATT ACGGGGT-CATAGTTCATAGCCCATATATGGAGTTC-CGCGTTACATAACTTACGGTA AATGGCCCGCCTGGCTGACCGCCCAAC-GACCCCCGCCCATTGACGTCAATAATGAC GTATGT-TCCCATAGTAACGCCAATAGGGACMTC-CATTGACGTCAATGGGTGGACTA TTTACGGTAAACTGCCCACTTGGCAGTA-CATCAAGTGTATCATATGCCAAGTACGCC CCCTAT-TGACGTCAATGACGGTAAATGGCCCGC-CTGGCATTATGCCCAGTACATGAC CTTATGGGACTTTCCTACTTGGCAGTA-CATCTACGTATTAGTCATCGCTATTACCATG GTGAT-GCGGTTTTGGCAGTACAT-CAATGGGCGTGGATAGCGGTTTGACTCACGGGGA TCCAAGTCTCCACCCCATTGACGT-CAATGGGAGTTTGTTTTGGCACCAAAATCAA CGG-GACTTTCCAAAATGTCGTAACAACTC-CGCCCCATTGACGCAAATGGGCGGTAG GCGTGTACGGTGGGAGGTCTATATAAG-CAGAGCTCTCTGGCTAACTAGAGAACCCA CTGCT-TACTGGCTTATCGAAATTAATACGACT-CACTATAGGGAGACCCAAGCTTGGT ACCGAGCTCGGATCgatctgggaaagcg-caagagagagcgcacacgcacacacccgccgcgcgcactcgg (SEQ ID No. 25).

In this construct, the flanking primer 1 and primer 2 sequences provide the recombination region which permits the insertion of the CMV promoter in front of the coding sequence for the human Shh gene. Other heterologous promoters (or other transcriptional regulatory sequences) can be inserted in a genomic hedgehog gene by a similar method.

In still other embodiments, the replacement region merely deletes a negative transcriptional control element of the native gene, e.g., to activate expression, or ablates a positive control element, e.g., to inhibit expression of the targeted gene.

V. Exemplary ptc Therapeutic Compounds.

In another embodiment, the subject method is carried out using a ptc therapeutic composition. Such compositions can be generated with, for example, compounds which bind to patched and alter its signal transduction activity, compounds which alter the binding and/or enzymatic activity of a protein (e.g., intracellular) involved in patched signal pathway, and compounds which alter the level of expression of a hedgehog protein, a patched protein or a protein involved in the intracellular signal transduction pathway of patched.

The availability of purified and recombinant hedgehog polypeptides facilitates the generation of assay systems which can be used to screen for drugs, such as small organic molecules, which are either agonists or antagonists of the normal cellular function of a hedgehog and/or patched protein, particularly their role in the pathogenesis of peripheral nerve proliferation and/or differentiation. In one embodiment, the assay evaluates the ability of a compound to modulate binding between a hedgehog polypeptide and a hedgehog receptor such as patched. In other embodiments, the assay merely scores for the ability of a test compound to alter the signal transduction acitity of the patched protein. In this manner, a variety of hedgehog and/or ptc therapeutics, both agonists (inhibit T-cell maturation) and antagonist (promote T-cell maturation) can be identified. A variety of assay formats will suffice and, in light of the present disclosure, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Acordingly, in an exemplary screening assay for ptc therapeutics, the compound of interest is contacted with a mixture including a hedgehog receptor protein (e.g., a cell expressing the patched receptor) and a hedgehog protein under conditions in which it is ordinarily capable of binding the hedgehog protein. To the mixture is then added a composition containing a test compound. Detection and quantification of receptor/hedgehog complexes provides a means for determining the test compound's efficacy at inhibiting (or potentiating) complex formation between the receptor protein and the hedgehog polypeptide. The efficacy of the compound can be assessed by generating dose response curves from data obtained using various concentrations of the test compound. Moreover, a control assay can also be performed to provide a baseline for comparison. In the control assay, isolated and purified hedgehog polypeptide is added to the receptor protein, and the formation of receptor/hedgehog complex is quantitated in the absence of the test compound.

In other embodiments, a ptc therapeutic of the present invention is one which disrupts the association of patched with smoothened.

Agonist and antagonists of peripheral nerve maintanence can be distinguished, and the efficacy of the compound can be assessed, by subsequent testing with T lymphocytes, e.g., in culture.

In an illustrative embodiment, the polypeptide utilized as a hedgehog receptor can be generated from the patched protein. Accordingly, an exemplary screening assay includes all or a suitable portion of the patched protein which can be obtained from, for example, the human patched gene (GenBank U43148) or other vertebrate sources (see GenBank Accession numbers U40074 for chicken patched and U46155 for mouse patched), as well as from *drosophila* (GenBank Accession number M28999) or other invertebrate sources. The patched protein can be provided in the screening assay as a whole protein (preferably expressed on the surface of a cell), or alternatively as a fragment of the full length protein which binds to hedgehog polypeptides, e.g., as one or both of the substantial extracellular domains (e.g. corresponding to residues Asn120-Ser438 and/or Arg770-Trp1027 of the human patched protein—which are also potential antagonists of hedgehog-dependent signal transduction). For instance, the patched protein can be provided in soluble form, as for example a preparation of one of the extracellular domains, or a preparation of both of the extracellular domains which are covalently connected by an unstructured linker (see, for example, Huston et al. (1988) *PNAS* 85:4879; and U.S. Pat. No. 5,091,513). In other embodiments, the protein can be provided as part of a liposomal preparation or expressed on the surface of a cell. The patched protein can derived from a recombinant gene, e.g., being ectopically expressed in a heterologous cell. For instance, the protein can be expressed on oocytes, mammalian cells (e.g., COS, CHO, 3T3 or the like), or yeast cell by standard recombinant DNA techniques. These recombinant cells can be used for receptor binding, signal transduction or gene expression assays. Marigo et al. (1996) *Development* 122: 1225–1233 illustrates a binding assay of human hedgehog to chick patched protein ectopically expressed in *Xenopus laevis* oocytes. The assay system of Marigo et al. can be adapted to the present drug screening assays. As illustrated in that reference, Shh binds to the patched protein in a selective, saturable, dose-dependent manner, thus demonstrating that patched is a receptor for Shh.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, for cell-free assays, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide, e.g. an $^{35}$S-labeled hedgehog polypeptide, and the test compound and incubated under conditions conducive to complex formation, e.g. at physiological conditions for salt and pH, though slightly more stringent conditions may be desired. Following incubation, the beads are washed to remove any unbound hedgehog polypeptide, and the matrix bead-bound radiolabel determined directly (e.g. beads placed in scintillant), or in the supernatant after the receptor/hedgehog complexes are dissociated. Alternatively, the complexes can be dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g. paranitrophenylphosphate. Likewise, a fusion protein comprising the hedgehog polypeptide and glutathione-5-transferase can be provided, and complex formation quantitated by detecting the GST activity using l-chloro-2,4-dinitrobenzene (Habig et al (1974) *J Biol Chem* 249:7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266: 21150–21157) which includes a 10-residue sequence from c-myc, as well as the pFLAG system (International Biotechnologies, Inc.) or the pEZZ-protein A system (Pharamacia, N.J.).

Where the desired portion of the hedgehog receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g. phosphatidylcholine liposomes) or in cell membrane-derived vesicles (see, for example, Bear et al. (1992) *Cell* 68: 809–818; Newton et al. (1983) *Biochemistry* 22: 6110–6117; and Reber et al. (1987) *J Biol Chem* 262: 11369–11374).

In addition to cell-free assays, such as described above, the readily available source of hedgehog proteins provided by the art also facilitates the generation of cell-based assays for identifying small molecule agonists/antagonists and the like. Analogous to the cell-based assays described above for screening combinatorial libraries, cells which are sensitive to hedgehog induction, e.g. patched-expressing cells or other myoblast-derived cells sensitive to hedgehog induction, can be contacted with a hedgehog protein and a test agent of interest, with the assay scoring for anything from simple binding to the cell to modulation in hedgehog inductive responses by the target cell in the presence and absence of the test agent. As with the cell-free assays, agents which produce a statistically significant change in hedgehog activities (either inhibition or potentiation) can be identified.

In other emdodiments, the cell-based assay scores for agents which disrupt association of patched and smoothened proteins, e.g., in the cell surface membrane or liposomal preparation.

In addition to characterizing cells that naturally express the patched protein, cells which have been genetically engineered to ectopically express patched can be utilized for drug screening assays. As an example, cells which either express low levels or lack expression of the patched protein, e.g. *Xenopus laevis* oocytes, COS cells or yeast cells, can be genetically modified using standard techniques to ectopically express the patched protein. (see Marigo et al., supra).

The resulting recombinant cells, e.g., which express a functional patched receptor, can be utilized in receptor binding assays to identify agonist or anatagonsts of hedgehog binding. Binding assays can be performed using whole cells. Furthermore, the recombinant cells of the present invention can be engineered to include other heterolgous genes encoding proteins involved in hedgehog-dependent siganl pathways. For example, the gene products of one or more of smoothened, costal-2 and/or fused can be co-expressed with patched in the reagent cell, with assays being sensitive to the functional reconstituion of the hedgehog signal transduction cascade.

Alternatively, liposomal preparations using reconstituted patched protein can be utilized. Patched protein purified from detergent extracts from both authentic and recombinant origins can be reconstituted in in artificial lipid vesicles (e.g. phosphatidylcholine liposomes) or in cell membrane-derived vesicles (see, for example, Bear et al. (1992) *Cell* 68: 809–818; Newton et al. (1983) *Biochemistry* 22: 6110–6117; and Reber et al. (1987) *J Biol Chem* 262: 11369–11374). The lamellar structure and size of the resulting liposomes can be characterized using electron microscopy. External orientation of the patched protein in the reconstituted membranes can be demonstrated, for example, by immunoelectron microscopy. The hedgehog protein binding activity of liposomes containing patched and liposomes without the protein in the presence of candidate agents can be compared in order to identify potential modulators of the hedgehog-patched interaction.

The hedgehog protein used in these cell-based assays can be provided as a purified source (natural or recombinant in origin), or in the form of cells/tissue which express the protein and which are co-cultured with the target cells. As in the cell-free assays, where simple binding (rather than induction) is the hedgehog activity scored for in the assay, the protein can be labelled by any of the above-mentioned techniques, e.g., fluorescently, enzymatically or radioactively, or detected by immunoassay.

In addition to binding studies, functional assays can be used to identified modulators, i.e., agonists or antagonists, of hedgehog or patched activities. By detecting changes in intracellular signals, such as alterations in second messengers or gene expression, in patched-expressing cells contacted with a test agent, candidate agonists and antagonists to patched signaling can be identified.

A number of gene products have been implicated in patched-mediated signal transduction, including patched, the transcription factor cubitus interruptus (ci), the serine/threonine kinase fused (fu) and the gene products of costal-2, smoothened and suppressor of fused.

The interaction of a hedgehog protein with patched sets in motion a cascade involving the activation and inhibition of downstream effectors, the ultimate consequence of which is, in some instances, a detectable change in the transcription or translation of a gene. Potential transcriptional targets of patched signaling are the patched gene itself (Hidalgo and Ingham, 1990 *Development* 110, 291–301; Marigo et al., 1996) and the vertebrate homologs of the *drosophila* cubitus interruptus gene, the GLI genes (Hui et al. (1994) *Dev Biol* 162: 402–413). Patched gene expression has been shown to be induced in cells of the limb bud and the neural plate that are responsive to Shh. (Marigo et al. (1996) *PNAS*, in press; Marigo et al. (1996) *Development* 122: 1225–1233). The GLI genes encode putative transcription factors having zinc finger DNA binding domains (Orenic et al. (1990) *Genes & Dev* 4: 1053–1067; Kinzler et al. (1990) *Mol Cell Biol* 10:6344642). Transcription of the GLI gene has been reported to be upregulated in response to hedgehog in limb buds, while transcription of the GLI3 gene is downregulated in response to hedgehog induction (Marigo et al. (1996) *Development* 122: 1225–1233). By selecting transcriptional regulatory sequences from such target genes, e.g. from patched or GLI genes, that are responsible for the up- or down regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as agonists or antagonists of ptc induction of differentiation/quiescence.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270: 10314–10322; and Kube et al. (1995) *Cytokine* 7: 1–7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsice to patched-dependent signalling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc therapeutic.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), *Nature* 282: 864–869) luciferase, and other enzyme detection systems, such as beta-galactosidase; firefly luciferase (deWet et al. (1987), *Mol. Cell. Biol.* 7: 725–737); bacterial luciferase (Engebrecht and Silverman (1984), *PNAS* 1: 4154–4158; Baldwin et al. (1984), *Biochemistry* 23: 3663–3667); alkaline phosphatase (Toh et al. (1989) *Eur. J. Biochem.* 182: 231–238, Hall et al. (1983) *J. Mol. Appl. Gen.* 2: 101), human placental secreted alkaline phosphatase (Cullen and Malim (1992) *Methods in Enzymol.* 216: 362–368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In yet other embodiments, second messenger generation can be measured directly in the detection step, such as mobilization of intracellular calcium, phospholipid metabolism or adenylate cyclase activity are quantitated, for instance, the products of phospholipid hydrolysis $IP_3$, DAG or cAMP could be measured For example, recent studies have implicated protein kinase A (PKA) as a possible component of hedgehog/patched signaling (Hammerschmidt et al. (1996) *Genes & Dev* 10:647). High PKA activity has been shown to antagonize hedgehog signaling in these systems. Although it is unclear whether PKA acts directly downstream or in parallel with hedgehog signaling, it is possible that hedgehog signalling occurs via inhibition of PKA activity. Thus, detection of PKA activity provides a potential readout for the instant assays.

In a preferred embodiment, the ptc therapeutic is a PKA inhibitor. A variety of PKA inhibitors are known in the art, including both peptidyl and organic compounds. For instance, the ptc therapeutic can be a 5-isoquinolinesulfonamide, such as represented in the general formula:

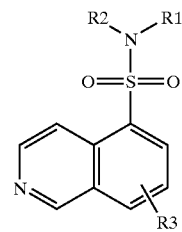

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, $(CH_2)_m$—$R_8$, $(CH_2)_m$—OH, —$(CH_2)_m$—O-lower alkyl, —$(CH_2)_m$—O-lower alkenyl —$(CH_2)_n$—O—C 10 $(CH_2)_m$—$R_8$, —$(CH_2)_m$—SH, —$(CH_2)_m$—S-lower alkyl, ——$(CH_2)_m$—S-lower alkenyl, —$(CH_2)_n$—S—$(CH_2)_m$-$R_8$ or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$-$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, ——$(CH_2)_n$—S—$(CH_2)_m$—$R_8$;

$R_8$ represents a substituted or unsubstituted aryl, aralkyl, cycloalkyl, cycloalkenyl, or heterocycle; and n and m are independently for each occurrence zero or an integer in the range of 1 to 6.

In a preferred embodiment, the PKA inhibitor is N-[2-((p-bromocinnamyl)amino)ethyl]-5-isoquinolinesulfonamide (H-89; Calbiochem Cat. No. 371963), e.g., having the formula:

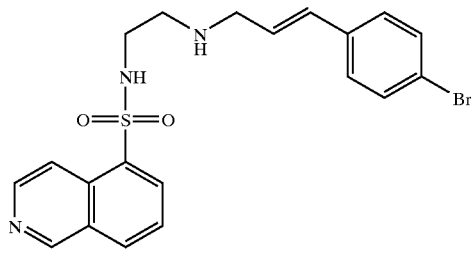

In another embodiment, the PKA inhibitor is 1-(5-isoquinolinesulfonyl)-2-methylpiperazine (H-7; Calbiochem Cat. No. 371955), e.g., having the formula:

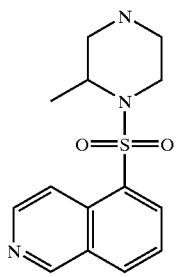

In still other embodiments, the PKA inhibitor is KT5720 (Calbiochem Cat. No. 420315), having the structure

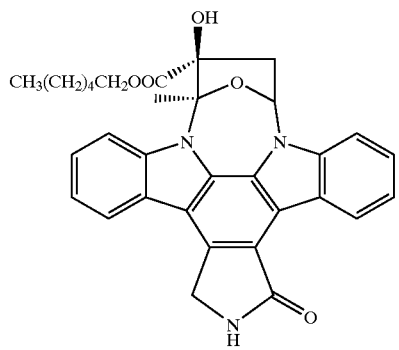

A variety of nucleoside analogs are also useful as PKA inhibitors. For example, the subject method can be carried out cyclic AMP analogs which inhibit the kinase activity of PKA, as for example, 8-bromo-cAMP or dibutyryl-cAMP

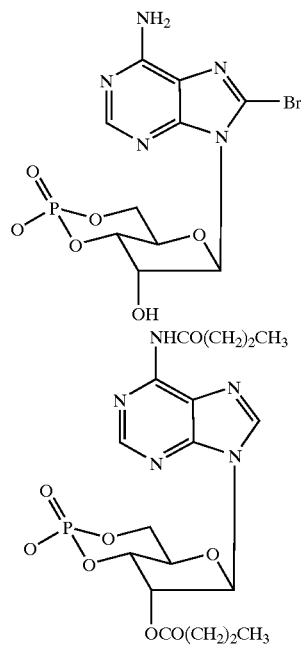

Exemplary peptidyl inhibitors of PKA activity include the PKA Heat Stable Inhibitor (isoform ca; see, for example, Calbiochem Cat. No. 539488, and Wen et al. (1995) *J Biol Chem* 270:2041).

Certain hedehog receptors may stimulate the activity of phospholipases. Inositol lipids can be extracted and analyzed using standard lipid extraction techniques. Water soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84: 45–56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the *drosophila* gene fused (fu) which encodes a serine/threonine kinase has been identified as a potential downstream target in hedgehog signaling. (Preat et al., 1990 *Nature* 347, 87–89; Therond et al. 1993, *Mech. Dev.* 44. 65–80). The ability of compounds to modulate serine/threonine kinase activation could be screened using colony immunoblotting (Lyons and Nelson (1984) *Proc. Natl. Acad. Sci. USA* 81: 7426–7430) using antibodies against phosphorylated serine or threonine residues. Reagents for performing such assays are commercially available, for example, phosphoserine and phosphothreonine specific antibodies which measure increases in phosphorylation of those residues can be purchased from comercial sources.

In yet another embodiment, the ptc therapeutic is an antisense molecule which inhibits expression of a protein involved in a patched-mediated signal transduction pathway. To illustrate, by inhibiting the expression of a protein which are involved in patched signals, such as fused, costal-2, smoothened and/or Gli genes, the ability of the patched signal pathway(s) to inhibit proliferation of a cell can be altered, e.g., potentiated or repressed.

As used herein, "antisense" therapy refers to administration or in situ generation of oligonucleotide probes or their derivatives which specifically hybridize (e.g. bind) under cellular conditions with cellular mRNA and/or genomic DNA encoding a hedgehog protein, patched, or a protein involved in patched-mediated signal transduction. The hybridization should inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the target cellular mRNA. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6: 958–976; and Stein et al. (1988) *Cancer Res* 48: 2659–2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25–26 mers. When testing an antisense oligonucleotide, a mismatched control can be constructed. The controls can be generated by reversing the sequence order of the corresponding antisense oligonucleotide in order to conserve the same ratio of bases.

In an illustrative embodiment, the ptc therapeutic can be an antisense construct for inhibiting the expression of patched, e.g., to mimic the inhibition of patched by hedgehog. Exemplary antisense constructs include:

5'-GTCCTGGCGCCGCCGCCGCCGTCGCC (SEQ ID No. 26)

5'-TTCCGATGACCGGCCTTTCGCGGTGA (SEQ ID No. 27)

5'-GTGCACGGAAAGGTGCAGGCCACACT (SEQ ID No. 28)

VI. Exemplary Pharmaceutical Preparations of Hedgehog and ptc Therapeutics

The source of the hedgehog and ptc therapeutics to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of a secreted protein and can be adapted for purification of hedgehog polypeptides. Recombinant sources of hedgehog polypeptides are also available. For example, the gene encoding hedgehog polypeptides, are known, inter alia, from PCT publications WO 95/18856 and WO 96/17924.

Those of skill in treating peripheral neuropathies can determine the effective amount of an hedgehog or ptc therapeutic to be formulated in a pharmaceutical or cosmetic preparation.

The hedgehog or ptc therapeutic formulations used in the method of the invention are most preferably applied in the form of appropriate compositions. As appropriate compositions there may be cited all compositions usually employed for systemically or topically administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular hedgehog or ptc therapeutic as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositons suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component.

As appropriate compositions for topical application there may be cited all compositions usually employed for topically administering therapeuitcs, e.g., creams, gellies, dressings, shampoos, tinctures, pastes, ointments, salves, powders, liquid or semiliquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, gellies, ointments and the like will conveniently be used.

It is especially advantageous to formulate the subject compositions in dosage unit form for ease of administration and uniformity of dosage. Dosage unit form as used in the specification and claims herein refers to physically discreate units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the many applications whcih can be considered cosmetic uses. Cosmetic compositions known in the art, preferably hypoallergic and pH controlled are especially preferred, and include toilet waters, packs, lotions, skin milks or milky lotions. The preparations contain, besides the hedgehog or ptc therapeutic, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the hedgehog or ptc therapeutic, will be incorporated in the compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, all % symbols refer to weight by weight percentage.

Particular compositions for use in the method of the present invention are those wherein the hedgehog or ptc therapeutic is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of a hedgehog polypeptide, are encapsulated in the aqueous spaces between the molecular layers. The lipid soluble active ingredient of hedgehog or ptc therapeutic, such as an organic mimetic, is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other artknown suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of hedgehog and ptc therapeutics is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated hedgehog or ptc therapeutic can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanol-amine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Apart from the above-described compositions, use may be made of covers, e.g. plasters, bandages, dressings, gauze pads and the like, containing an appropriate amount of a hedgehog or ptc therapeutic. In some cases use may be made of plasters, bandages, dressings, gauze pads and the like which have been impregnated with a topical formulation containing the therapeutic formulation.

VII. Exemplary Hedgehog Antagonists

Exemplary hedgehog antagonists of the invention include cyclopamine, tomatidine, jervine, AY9944, triparanol, forskolin, cAMP, dibutyryl cAMP (and other hydrophobically modified cAMP variants) and fuctionally effective derivatives thereof. Additional hedgehog antagonists, functionally effective derivatives, compositions and methods for making such compounds are described in detail in the following U.S. patent applications: Baxter et al., 09/663, 835; Beachy et al. entitled "Inhibitors of hedgehog signaling pathways, compositions and uses related thereto" filed Oct. 10, 2000; Baxter et al. "Mediators of hedgehog signaling pathway, compositions and uses related thereto" filed Oct. 13, 2000; Philip Beachy, "Regulators of the hedgehog pathway, compositions and uses related thereto" filed Oct. 13, 2000.

Evaluation of the Effects of Hedgehog on T-Cell Development

The invention now being generally described, it will be more readily understood by reference to the following examples which are included merely for purposes of illustration of certain aspects and embodiments of the present invention, and are not intended to limit the invention.

Figure 2:
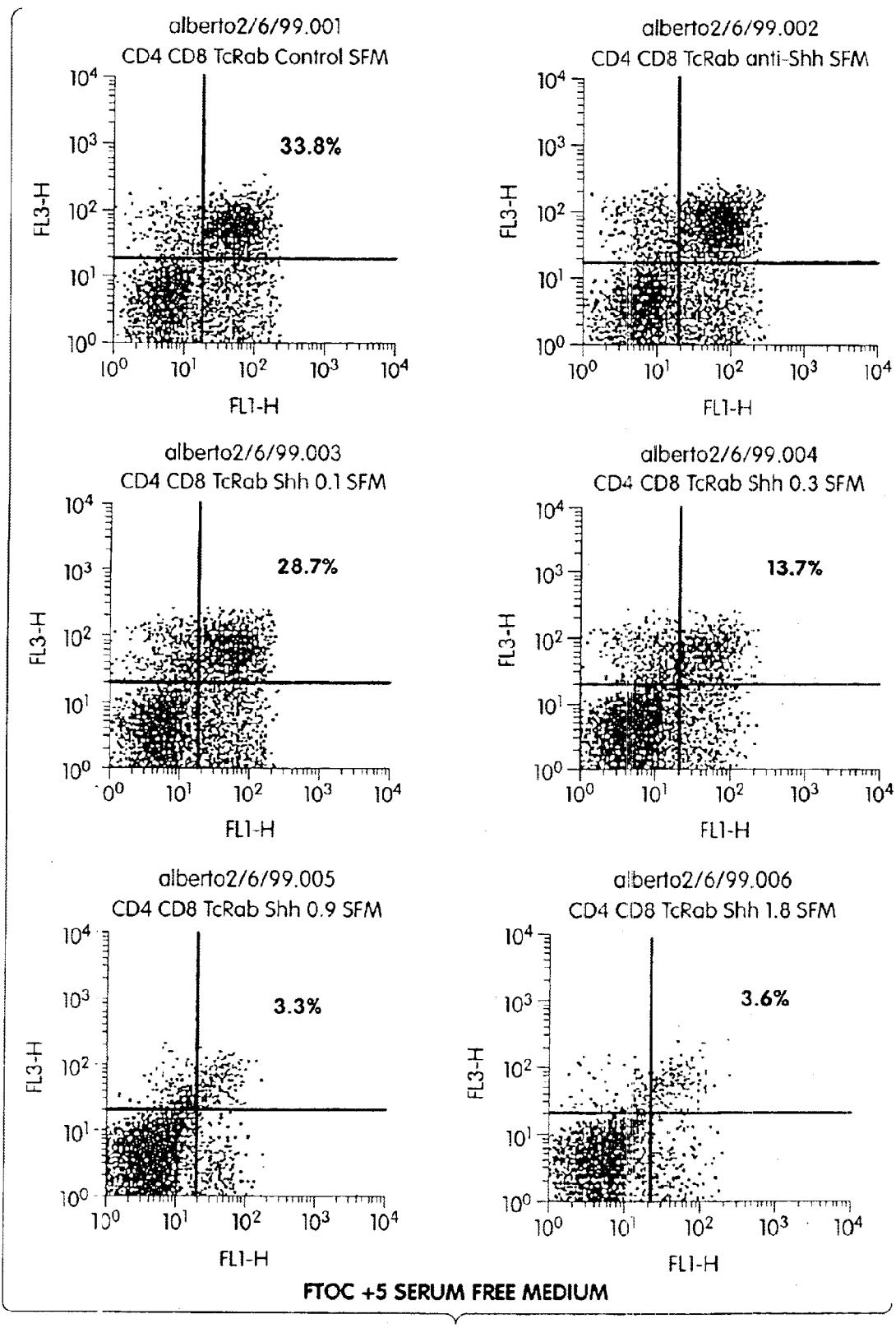
Figure 3:
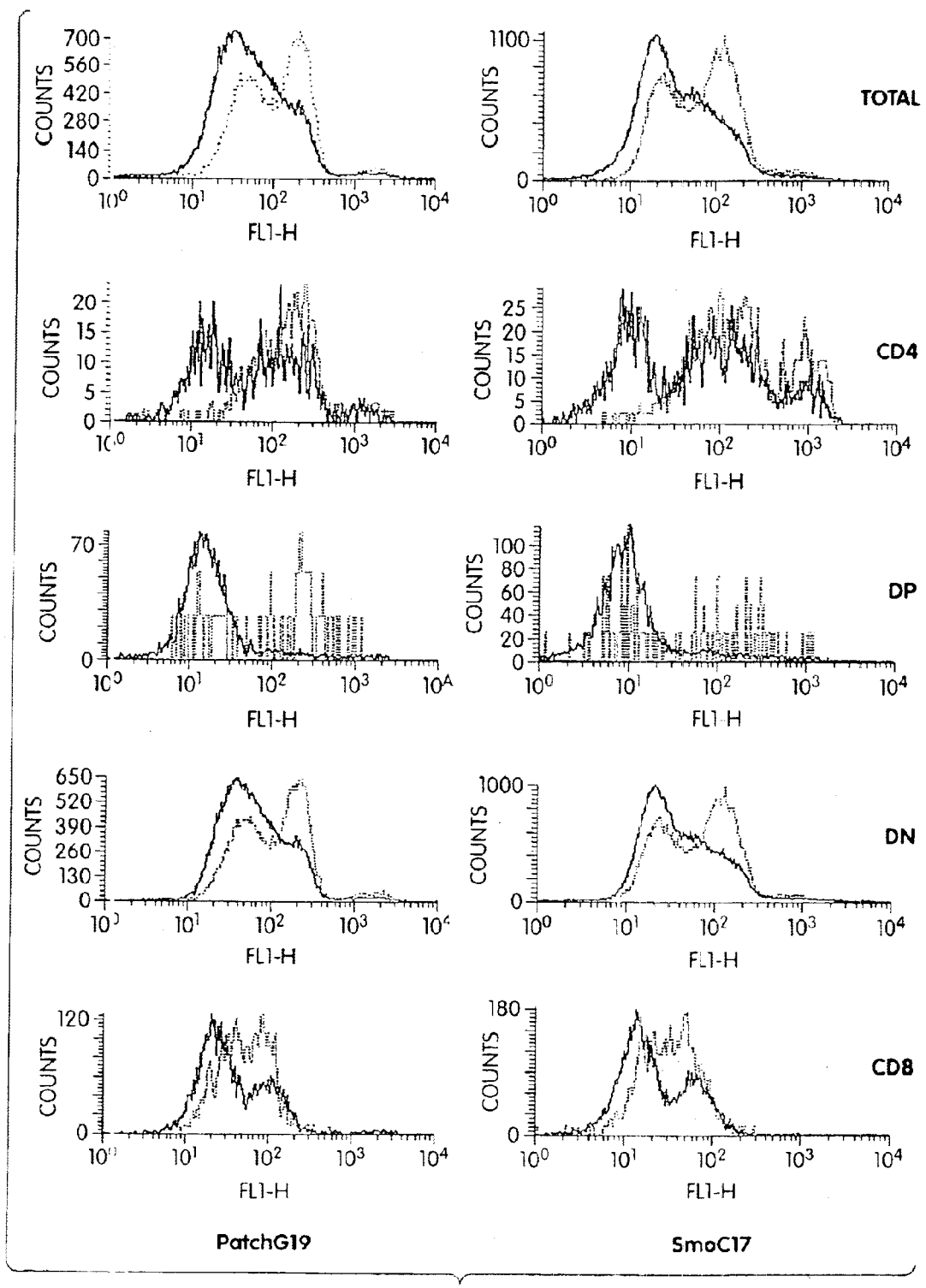
Figure 4:
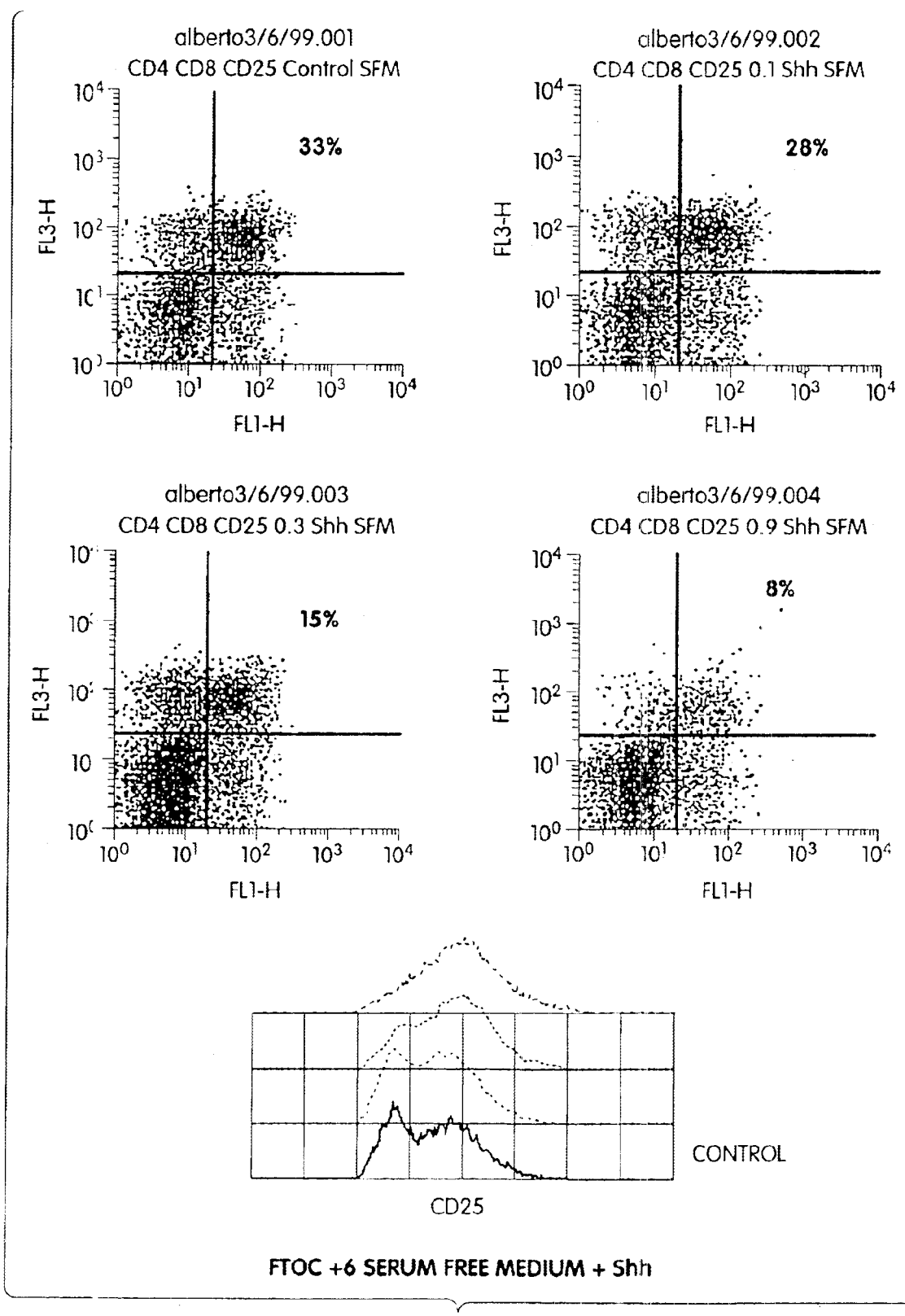

Utilizing a fetal thymic organ culture, the effects of Shh on T-cell maturation was detemined. Briefly, immature thymocytes (CD4-/CD8-[DN]) were isolated from E14 thymus. The cells were culture for about 7 days, and the level of mature thymocytes, e.g., CD4+/CD8+[DP], was assessed. In certain cultures, octyl-modifed Shh was added to the culture; in other cultures, the anti-hedgehog 5E1 antibody was added. As illustrated in FIGS. 1–4, the addition of Shh to the culture resulted in an increase in the percentage of cells after 7 days with markers indicative of immature thymocytes. Conversely, addition of the 5E1 antibody resulted in an increase in the percentage of mature T lymphocytes after 7 days.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

I claim:

1. A method for suppressing thymic T cell maturation of an animal, comprising administering to the animal an amount of a polypeptide that includes an N-terminal auto-proteolytic fragment of a hedgehog polypeptide, effective to suppress thymic T cell maturation, wherein the hedgehog polypeptide includes an amino acid sequence selected from SEQ ID Nos. 10–18 and binds to a patched polypeptide.

2. A method for suppressing T cell maturation in the thymus, comprising contacting the T cell with an amount of a polypeptide that includes an N-terminal auto-proteolytic fragment of a hedgehog polypeptide effective to suppress T cell maturation in the thymus, wherein the hedgehog polypeptide includes an amino acid sequence selected from SEQ ID Nos. 10–18, and binds to a patched polypeptide.

3. The method of claim 1 or 2, wherein the hedgehog amino acid sequence is identical to at least one of SEQ ID Nos. 10–18.

4. The method of claim 1, or 2, wherein the polypeptide is encodable by a nucleic acid which hybridizes under stringent conditions of 6.0× sodium chloride/sodium citrate (SSC) at about 45° C., followed by a wash of 2.0×SSC at 50° C., to at least one of SEQ ID Nos. 1–9.

5. The method of claim 1 or 2, wherein the hedgehog polypeptide is a vertebrate hedgehog polypeptide.

6. The method of claim 5, wherein the polypeptide includes at least an N-terminal fragment of a vertebrate hedgehog polypeptide corresponding to residues 24–194 of SEQ ID No: 15.

7. The method of claim 1 or 2, wherein the polypeptide is modified with one or more lipophilic moieties.

8. The method of claim 7, wherein the polypeptide is modified with one or more sterol moieties.

9. The method of claim 8, wherein the sterol moiety is cholesterol.

10. The method of claim 7, wherein the polypeptide is modified with one or more fatty acid moieties.

11. The method of claim 10 wherein each fatty acid moiety is independently selected from myristoyl, palmitoyl, stearoyl, and arachidoyl.

12. The method of claim 7 wherein the polypeptide is modified with one or more aromatic hydrocarbons.

13. The method of claim 12 wherein each aromatic hydrocarbon is independently selected from benzene, perylene, phenanthrene, anthracene, naphthalene, pyrene, chrysene, and naphthacene.

14. The method of claim 7, wherein the polypeptide is modified one or more times with a C7–C30 alkyl or cycloalkyl.

15. The method of claim 1 or 2, wherein the polypeptide binds to patched and mimics hedgehog signal transduction by altering the localization, protein—protein binding, and/or enzymatic activity of an intracellular protein involved in hedgehog signaling.

* * * * *